(12) United States Patent
Newman et al.

(10) Patent No.: US 10,398,858 B2
(45) Date of Patent: Sep. 3, 2019

(54) SAFETY NEEDLE ASSEMBLY

(71) Applicant: Becton, Dickinson and Company, Franklin Lakes, NJ (US)

(72) Inventors: Craig Newman, Montvale, NJ (US); Stephen Richards, Carrywood, ID (US); Vadim Goykhman, Riverdale, NJ (US); Tieming Ruan, Belmont, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 127 days.

(21) Appl. No.: 15/473,275

(22) Filed: Mar. 29, 2017

(65) Prior Publication Data

US 2017/0203049 A1 Jul. 20, 2017

Related U.S. Application Data

(62) Division of application No. 12/922,776, filed as application No. PCT/US2009/037115 on Mar. 13, 2009, now Pat. No. 9,642,971.

(Continued)

(51) Int. Cl.
*A61M 5/50* (2006.01)
*A61M 5/32* (2006.01)
*A61M 5/34* (2006.01)

(52) U.S. Cl.
CPC .......... *A61M 5/5086* (2013.01); *A61M 5/326* (2013.01); *A61M 5/3293* (2013.01);
(Continued)

(58) Field of Classification Search
CPC .. A61M 5/321; A61M 5/3243; A61M 5/3245; A61M 5/3257; A61M 5/326;
(Continued)

(56) References Cited

U.S. PATENT DOCUMENTS 4,894,055 A 1/1990 Sudnak
4,897,083 A 1/1990 Martell
(Continued)

FOREIGN PATENT DOCUMENTS

DE 8909799 U1 11/1989
DE 102006022081 B3 1/2008
(Continued)

OTHER PUBLICATIONS

Clickfine(R) AutoProtect(TM); YPSOMED Selfcare Solutions; www.ypsomed.com/b2b@ypsomed.com.

*Primary Examiner* — Kami A Bosworth
(74) *Attorney, Agent, or Firm* — Dickinson Wright PLLC

(57) ABSTRACT

A safety needle assembly, including a hub; a needle fixed to the hub, the needle having a distal end and a proximal end; first and second shields, each having a tubular body at least partially encircling a portion of the needle, wherein in an initial state, the first shield extends from the hub; a biasing element disposed to urge the second shield distally toward the distal end of the needle; and a releasable retaining arrangement for releasably retaining the second shield in a first state. Upon a predetermined extent of proximal movement of the first shield relative to the hub, the second shield is released, thereby allowing the biasing element to urge the second shield to a second state in which the distal end of the needle is covered.

14 Claims, 32 Drawing Sheets

Related U.S. Application Data

(60) Provisional application No. 61/084,750, filed on Jul. 30, 2008, provisional application No. 61/081,878, filed on Jul. 18, 2008, provisional application No. 61/055,686, filed on May 23, 2008, provisional application No. 61/036,299, filed on Mar. 13, 2008.

(52) U.S. Cl.
CPC ..... *A61M 5/347* (2013.01); *A61M 2005/3247* (2013.01); *A61M 2005/3254* (2013.01); *A61M 2005/3263* (2013.01)

(58) Field of Classification Search
CPC .............. A61M 5/3269; A61M 5/3271; A61M 5/3275; A61M 5/5086; A61M 2005/3247; A61M 2005/3258; A61M 2005/3263; A61M 2005/3267; A61M 2005/3268; A61M 25/0612; A61M 25/0618; A61M 25/0625; A61M 25/0631; A61M 5/3268
See application file for complete search history.

(56) References Cited

U.S. PATENT DOCUMENTS

| | | |
|---|---|---|
| 4,998,924 A | 3/1991 | Ranford |
| 5,061,246 A | 10/1991 | Anapliotis |
| 5,193,552 A | 3/1993 | Columbus et al. |
| 5,246,428 A | 9/1993 | Falknor |
| 5,250,037 A | 10/1993 | Bitdinger |
| 5,256,153 A | 10/1993 | Hake |
| 5,269,765 A | 12/1993 | Kuracina |
| 5,279,579 A | 1/1994 | D'Amico |
| 5,292,314 A | 3/1994 | D'Alessio et al. |
| 5,336,197 A | 8/1994 | Kuracina et al. |
| 5,364,362 A | 11/1994 | Shulz |
| 5,389,085 A | 2/1995 | D'Alessio et al. |
| 5,417,662 A | 5/1995 | Hjertman et al. |
| 5,429,612 A | 7/1995 | Berthier |
| 5,514,097 A | 5/1996 | Knauer |
| 5,562,624 A | 10/1996 | Righi et al. |
| 5,591,138 A | 1/1997 | Vaillancourt |
| 5,609,577 A | 3/1997 | Haber et al. |
| 5,634,906 A | 6/1997 | Haber et al. |
| 5,688,241 A | 11/1997 | Asbaghi |
| 5,795,336 A | 8/1998 | Romano et al. |
| 5,810,775 A | 9/1998 | Shaw |
| 5,873,856 A | 2/1999 | Hjertman et al. |
| 5,971,966 A | 10/1999 | Lav |
| RE36,398 E | 11/1999 | Byrne et al. |
| 5,984,899 A | 11/1999 | D'Alessio et al. |
| RE36,447 E | 12/1999 | Byrne et al. |
| 6,017,329 A | 1/2000 | Hake |
| 6,110,147 A | 8/2000 | Perouse |
| 6,203,529 B1 | 3/2001 | Gabriel et al. |
| 6,224,576 B1 | 5/2001 | Thorne et al. |
| 6,379,336 B1 | 4/2002 | Asbaghi et al. |
| 6,547,764 B2 | 4/2003 | Larsen et al. |
| 6,569,124 B1 | 5/2003 | Perouse |
| 6,692,463 B1 | 2/2004 | Marteau et al. |
| 6,773,415 B2 | 8/2004 | Heiniger |
| 6,796,967 B2 | 9/2004 | Jensen |
| 6,855,129 B2 | 2/2005 | Jensen et al. |
| 6,939,330 B1 | 9/2005 | McConnell-Montalvo et al. |
| 6,986,760 B2 | 1/2006 | Giambattista et al. |
| 7,066,907 B2 | 6/2006 | Crossman et al. |
| 7,074,211 B1 | 7/2006 | Heininger et al. |
| 7,147,624 B2 | 12/2006 | Hirsiger et al. |
| 7,198,617 B2 | 4/2007 | Millerd |
| 7,229,432 B2 | 6/2007 | Marshall et al. |
| 7,278,986 B1 | 10/2007 | Frost |
| 7,361,160 B2 | 4/2008 | Hommann et al. |
| 7,361,166 B2 | 4/2008 | Bosse et al. |
| 7,370,759 B2 | 5/2008 | Hommann |
| 7,374,558 B2 | 5/2008 | Kirchhofer |
| 7,384,414 B1 | 6/2008 | Marshall et al. |
| 7,442,185 B2 | 10/2008 | Amark et al. |
| 7,635,350 B2 | 12/2009 | Scherer |
| 8,075,522 B2 * | 12/2011 | Larsen ................ A61M 5/326 604/110 |
| 8,177,745 B2 | 5/2012 | Brechbuehler et al. |
| 2002/0193746 A1 | 12/2002 | Chevallier |
| 2003/0014018 A1 | 1/2003 | Giambattista et al. |
| 2003/0060776 A1 | 3/2003 | Heiniger |
| 2003/0120209 A1 | 6/2003 | Jensen et al. |
| 2004/0122379 A1 | 6/2004 | Bosse et al. |
| 2005/0096597 A1 | 5/2005 | Crawford |
| 2005/0096599 A1 | 5/2005 | Crawford |
| 2005/0113750 A1 | 5/2005 | Targell |
| 2005/0267410 A1 | 12/2005 | Koska |
| 2005/0277893 A1 | 12/2005 | Liversidge |
| 2005/0288607 A1 | 12/2005 | Konrad |
| 2006/0095010 A1 | 5/2006 | Westbye |
| 2006/0270984 A1 | 11/2006 | Hommann |
| 2007/0027430 A1 | 2/2007 | Hommann |
| 2007/0129674 A1 | 6/2007 | Liversidge |
| 2007/0156101 A1 | 7/2007 | Liversidge |
| 2007/0173772 A1 | 7/2007 | Liversidge |
| 2007/0255225 A1 | 11/2007 | Alchas et al. |
| 2008/0009807 A1 | 1/2008 | Hommann |
| 2008/0071225 A1 | 3/2008 | Hommann et al. |
| 2008/0077093 A1 | 3/2008 | Gratwohl et al. |
| 2008/0103453 A1 | 5/2008 | Liversidge |
| 2008/0103454 A1 | 5/2008 | Gratwohl et al. |
| 2008/0249477 A1 | 10/2008 | Paproski et al. |
| 2008/0255526 A1 | 10/2008 | Bosse et al. |
| 2008/0262436 A1 | 10/2008 | Olson |
| 2008/0269691 A1 | 10/2008 | Cowe |
| 2009/0005742 A1 | 1/2009 | Liversidge |
| 2009/0221972 A1 | 9/2009 | Gratwohl et al. |
| 2009/0259178 A1 | 10/2009 | Brechbuehler et al. |
| 2009/0259196 A1 | 10/2009 | Gratwohl et al. |
| 2010/0114035 A1 | 5/2010 | Schubert et al. |
| 2010/0234811 A1 * | 9/2010 | Schubert ............... A61M 5/326 604/198 |
| 2011/0245770 A1 * | 10/2011 | Carrel ................... A61M 5/326 604/117 |

FOREIGN PATENT DOCUMENTS

| | | |
|---|---|---|
| DE | 102006041810 A1 | 3/2008 |
| EP | 1464353 A1 | 10/2004 |
| EP | 1747789 A2 | 1/2007 |
| EP | 1949929 A | 7/2008 |
| EP | 1949929 A1 | 7/2008 |
| FR | 2617718 A1 | 1/1989 |
| FR | 2881053 A1 | 7/2006 |
| WO | WO-9002515 A1 | 3/1990 |
| WO | WO-9209319 A1 | 6/1992 |
| WO | WO-9220281 A1 | 11/1992 |
| WO | WO-0191837 A1 | 12/2001 |
| WO | WO-0193924 A1 | 12/2001 |
| WO | WO-03045480 A1 | 6/2003 |
| WO | WO-03045481 A1 | 6/2003 |
| WO | WO-2003045481 A1 | 6/2003 |
| WO | WO-03105935 A2 | 12/2003 |
| WO | WO-2004000397 A1 | 12/2003 |
| WO | WO-2004030539 A1 | 4/2004 |
| WO | WO-2004071560 A1 | 8/2004 |
| WO | WO-2005097238 A2 | 10/2005 |
| WO | WO-2006018626 A1 | 2/2006 |
| WO | WO-2006072807 A1 | 7/2006 |
| WO | WO-2006111862 A1 | 10/2006 |
| WO | WO-2007077463 A1 | 7/2007 |
| WO | WO-2008025179 A1 | 3/2008 |
| WO | WO-2008028304 A1 | 3/2008 |
| WO | WO-2008028305 A1 | 3/2008 |
| WO | WO-2008028312 A1 | 3/2008 |
| WO | WO-2008035122 A1 | 3/2008 |
| WO | WO-2008043188 A1 | 4/2008 |
| WO | WO-2008044067 A1 | 4/2008 |
| WO | WO-2008050158 A2 | 5/2008 |
| WO | WO-2008083037 A1 | 7/2008 |
| WO | WO-2009003300 A1 | 1/2009 |

(56) References Cited

FOREIGN PATENT DOCUMENTS

| | | |
|---|---|---|
| WO | WO-2009030056 A1 | 3/2009 |
| WO | WO-2009114762 A1 | 9/2009 |
| WO | WO-2009114777 A1 | 9/2009 |
| WO | WO-2010126432 A1 | 11/2010 |

* cited by examiner

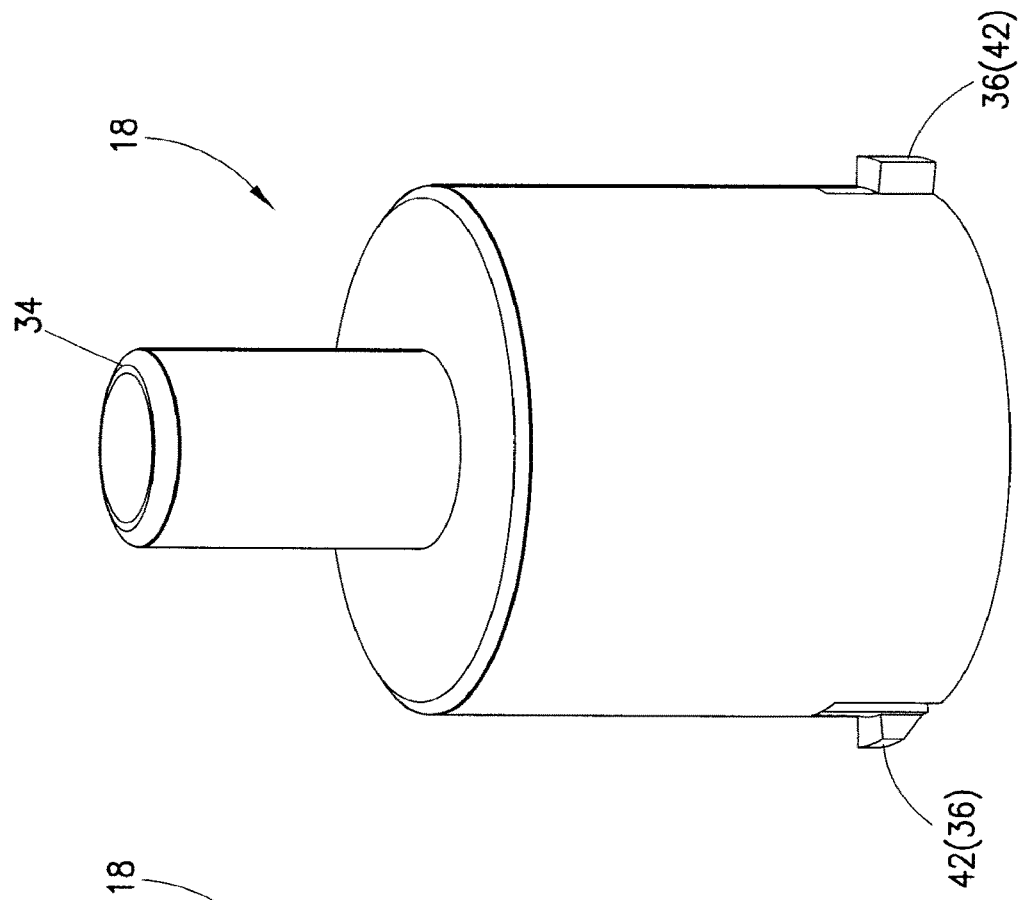
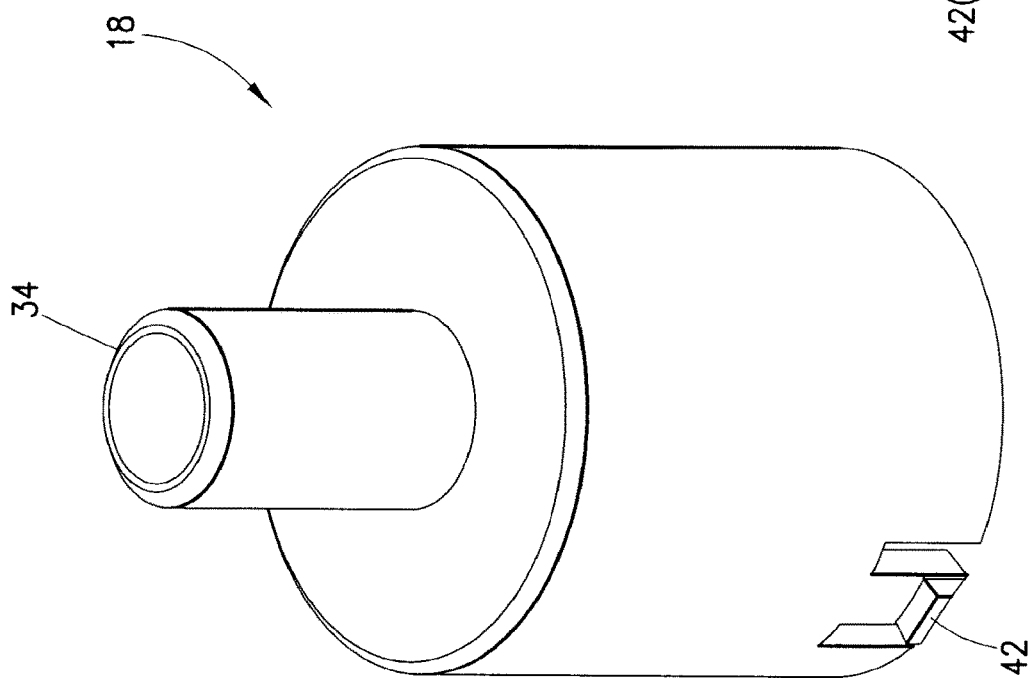

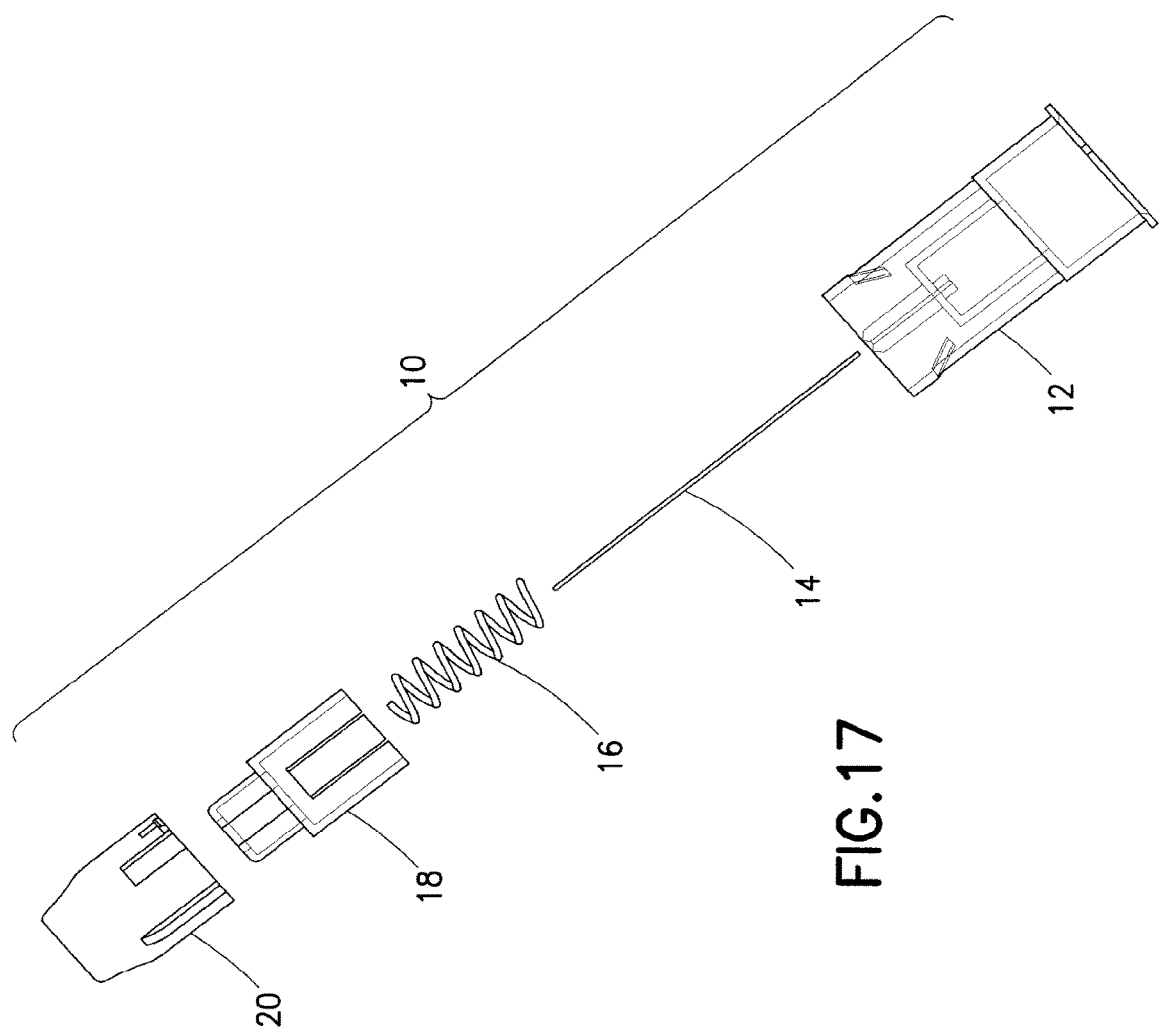

SAFETY NEEDLE ASSEMBLY

RELATED APPLICATIONS

This application is a division of U.S. patent application Ser. No. 12/922,776, filed on Aug. 16, 2011 and issued as U.S. Pat. No. 9,642,971 on May 9, 2018, which is the U.S. national stage of international patent application number PCT/US2009/037115, filed on Mar. 13, 2009, which claims the benefit of U.S. provisional patent application Ser. No. 61/084,750, filed on Jul. 30, 2008, U.S. provisional patent application Ser. No. 61/081,878, filed on Jul. 18, 2008, U.S. provisional patent application Ser. No. 61/055,686, filed on May 23, 2008, and U.S. provisional patent application Ser. No. 61/036,299, filed on Mar. 13, 2008. Each of the disclosures of these applications is hereby incorporated herein by reference in its entirety.

BACKGROUND OF THE INVENTION

Safety needle assemblies are known in the prior art for providing shielding to a used needle to prevent inadvertent "needle sticks" therewith. These assemblies may be "passive", which operate through normal use of the associated injector, or "active", which require an additional step or steps to operate beyond normal operation of the associated injector.

With respect to pen injectors which use pen needles, passive safety pen needle assemblies have been developed in the prior art which utilize a trigger that is activated upon sufficient application of force thereto during an injection procedure. A trigger may be provided which presses against a patient's skin with sufficient displacement of the trigger causing the assembly to activate. The activation of the trigger results in some form of a shield being released which may move distally to a shielding position covering a used needle. With these designs, concerns exist of preventing inadvertent trigger activation.

SUMMARY OF EMBODIMENTS OF THE INVENTION

A safety needle assembly is provided herein which includes a hub; a needle fixed to the hub; a first shield having a tubular body at least partially encircling a portion of the needle, wherein in an initial state, the first shield extends from the hub; a second shield having a tubular body at least partially encircling a portion of the needle; a biasing element disposed to urge the second shield distally towards a distal end of the needle; and, a releasable retaining arrangement for releasably retaining the second shield in a first state. Upon a predetermined extent of proximal movement of the first shield relative to the hub, the second shield is released to a second state in which the distal end of the needle is covered. Advantageously, two shields are provided for at least partially covering a needle with one of the shields acting as a trigger.

These and other features of the invention will be better understood through a study of the following detailed description and accompanying drawings.

BRIEF DESCRIPTION OF THE DRAWINGS

FIGS. 1-11 depict various aspects of a first embodiment of the subject invention;
FIGS. 15-42 depict various aspects of a second embodiment of the subject invention.

DETAILED DESCRIPTION OF EMBODIMENTS OF THE PRESENT INVENTION

Figure 1:
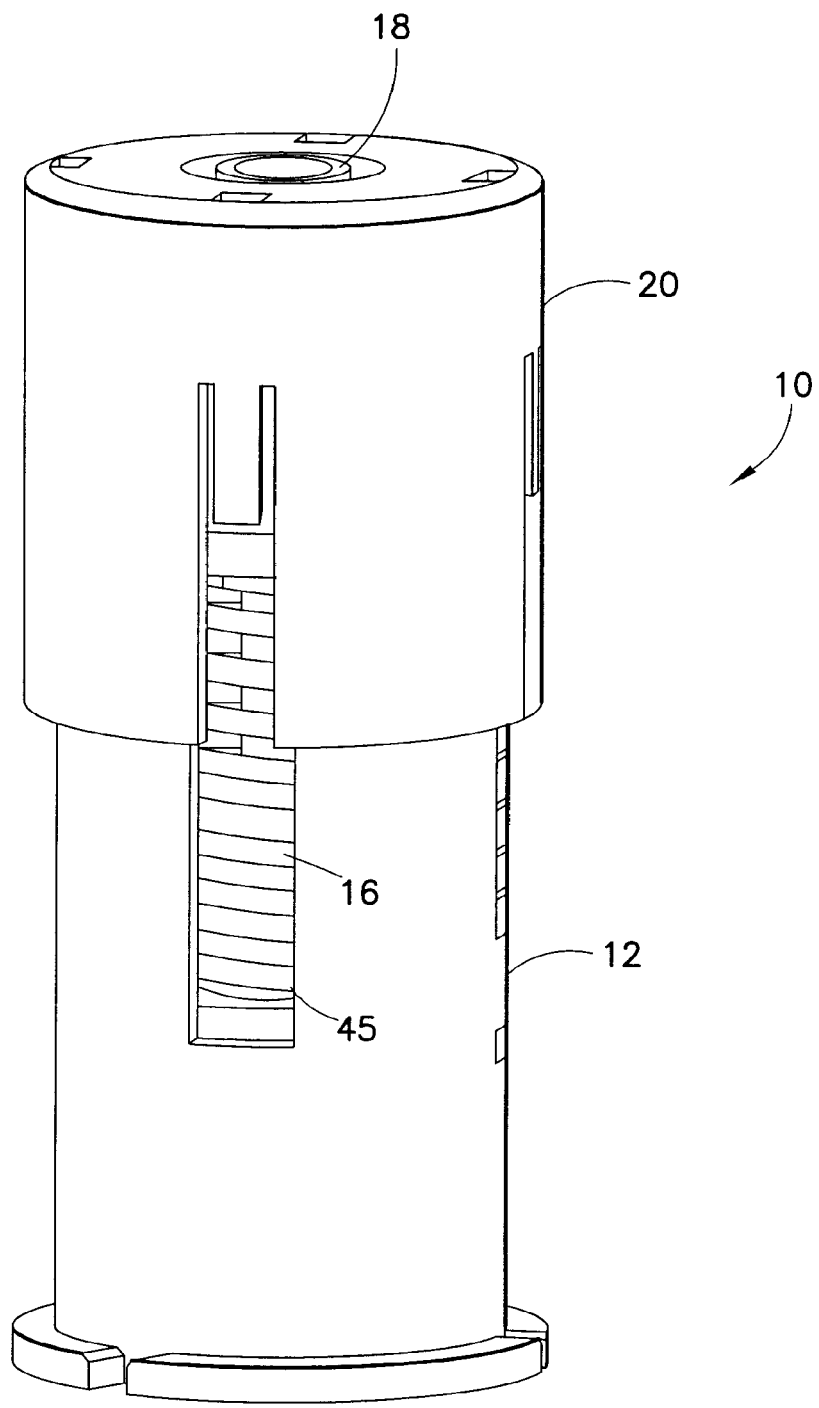
Figure 2:
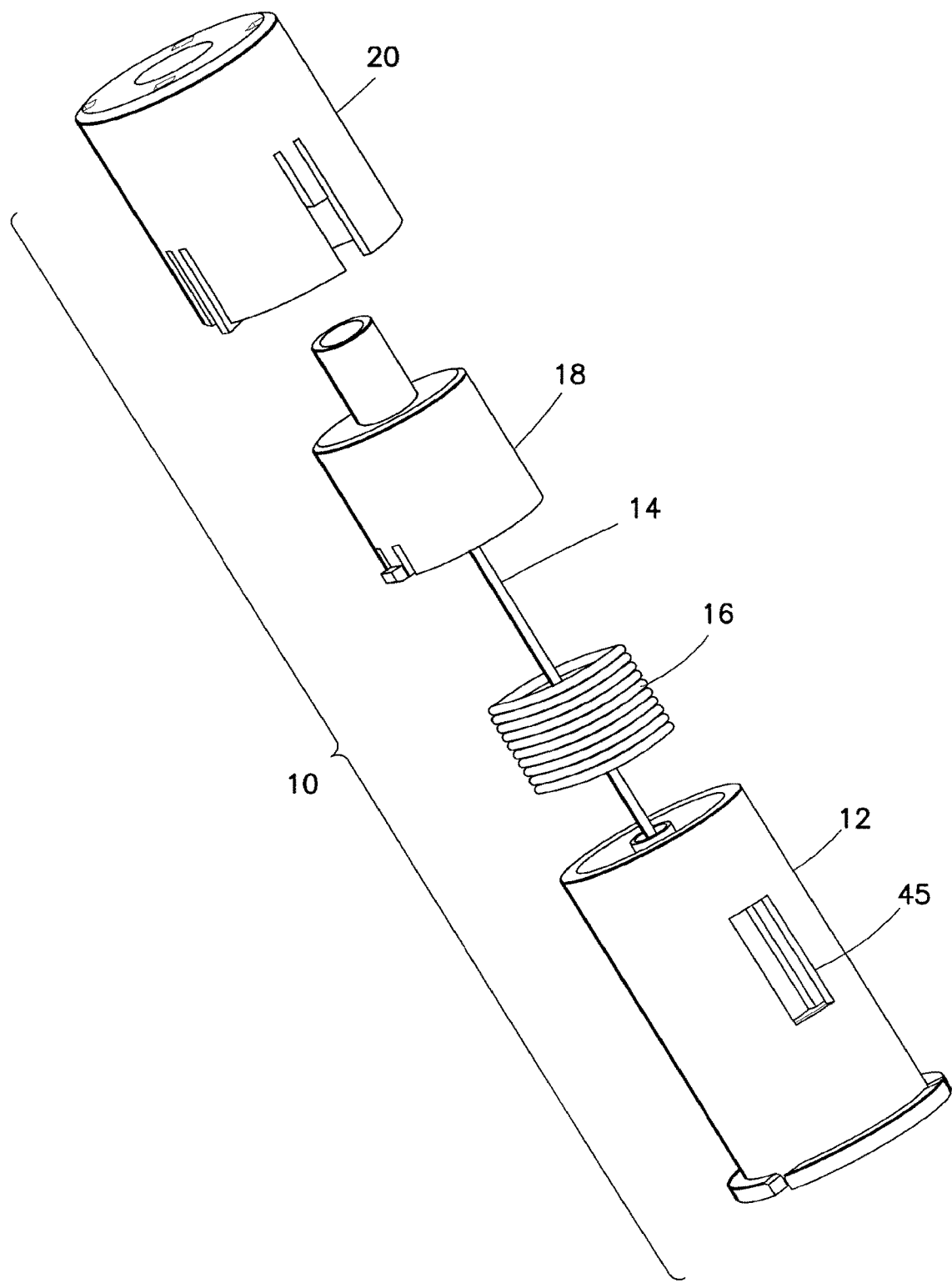

With reference to the Figures, a safety needle assembly 10 is provided herein. The assembly 10 generally includes a hub 12, a needle 14, a spring 16, a first shield 18 and a second shield 20. As described below, the assembly 10 is configured to shield a distal end of the needle 14 to prevent inadvertent needle sticks. The assembly 10 is particularly well-suited for use with pen injectors as a safety pen needle assembly.

The hub 12 includes a tubular body 22 which extends between a distal end 24 and a proximal end 26. In proximity to the proximal end 26, one or more features 28 may be provided for cooperative engagement with mounting features provided on an associated injector body, such as a pen injector body. The features 28 may be releasable mounting features (e.g., threads) and/or shape configuration(s) (e.g., taper corresponding to a Leur tip).

The needle 14 may be of any known type and includes a distal end 30, formed for insertion into a patient, and a proximal end 32. The needle 14 is mounted to the hub 12 using any known technique.

The first shield 18 is formed to at least partially encircle a portion of the needle 14. The second shield 20 is also formed to at least partially encircle a portion of the needle 14 with at least portions of the second shield 20 being located further radially outwardly from the needle 14 than the first shield 18.

The spring 16 is disposed to urge the first shield 18 distally, i.e., in a direction towards the distal end 30 of the needle 14. As used herein, "distally", or derivatives thereof, refers to a direction towards an injection site, while "proximally", or derivatives thereof, refers to a direction away from an injection site.

In operation, the first shield 18 and/or second shield 20 is urged distally by the spring 16. The second shield 20 may be urged distally under force of the spring 16 with the force of the spring 16 being transmitted to the second shield 20 via the first shield 18. The first shield 18 and/or second shield 20 is urged to a shielding position where the distal end 30 of the needle 14 is covered. The first shield 18 and/or second shield 20 is preferably locked in the shielding position.

It is preferred that the assembly 10 be activated passively. To obtain passive actuation, one of the first shield 18 or the second shield 20 is used as a trigger for actuation. In a first embodiment of the subject invention, the first shield 18 acts as a trigger, while in a second embodiment of the subject invention, the second shield 20 acts as a trigger.

Figure 3:
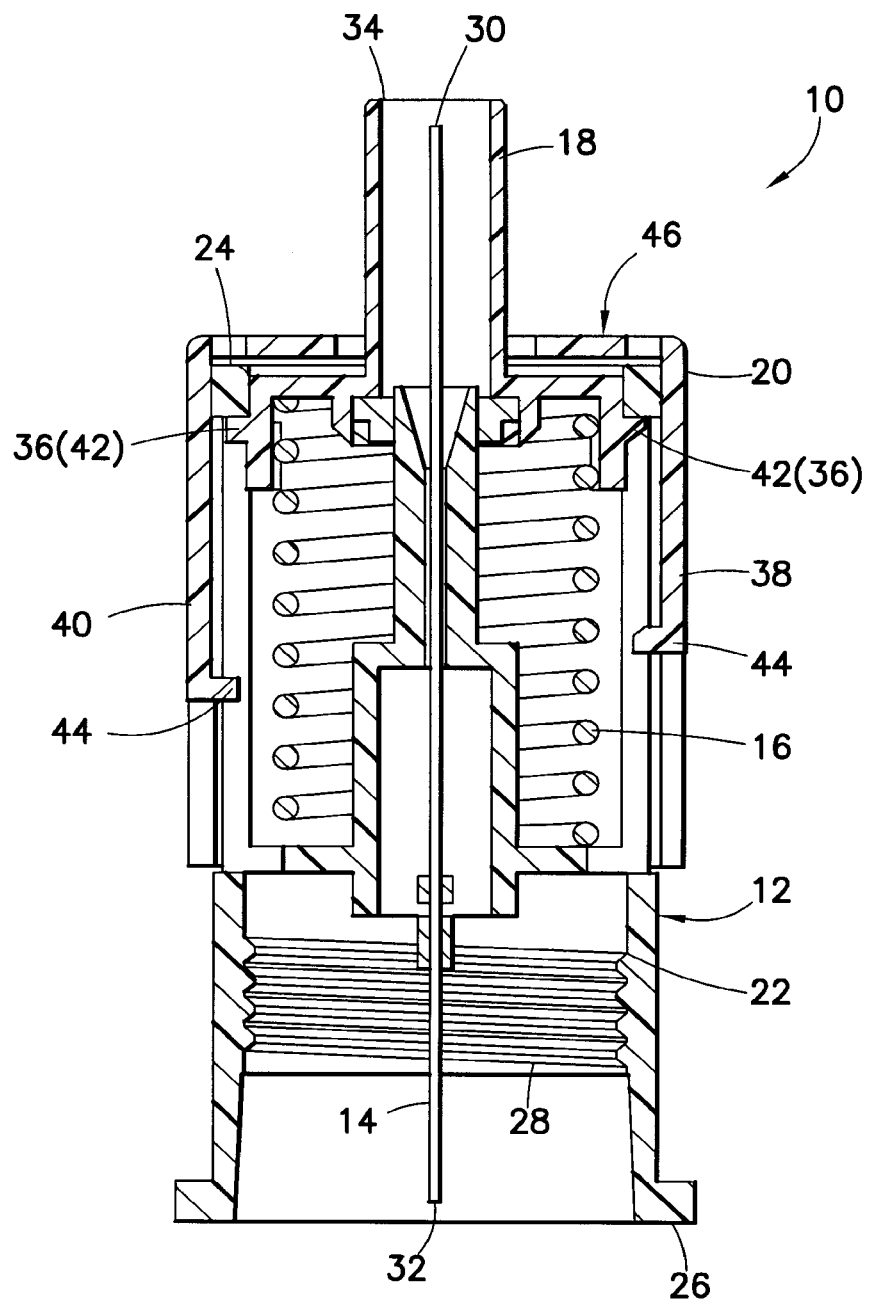

With reference to FIGS. 1-11, the first embodiment of the invention is depicted. Here, as best shown in FIG. 3, a portion of the first shield 18 extends distally beyond the hub 12 and the second shield 20. The first shield 18 terminates at a skin engaging surface 34 which is preferably located at the distal most portion of the first shield 18. During an injection procedure, the skin engaging surface 34 presses against a patient's skin and, with insertion of the needle 14 into the skin, the first shield 18 is caused to move proximally relative to the needle 14. In an initial state, the skin engaging surface 34 may be located distally of the distal end 30 of the needle 14 or may be located at a location along the length of the needle 14 to permit exposure of the distal end 30. Initial exposure of the distal end 30 may be desired to permit pre-injection visual inspection of the distal end 30, for example for priming.

As shown in FIG. 3, the spring 16 applies an urging force to the first shield 18 to position the first shield 18 in the initial position. One or more projections 36 may be provided on the first shield 18 to catch against the hub 12 to limit the distal extent of movement of the first shield 18 under force of the spring 16.

It is preferred that the second shield 20 be retained in a first, initial position in which the distal end 30 of the needle 14 is not covered by the second shield 20. It is preferred that the second shield 20 be releasably retained in the initial position. Any known configuration for obtaining releasable retention may be utilized including the provision of cooperating elements on the hub 12 and the second shield 20 and/or an interference fit between the hub 12 and the second shield 20.

Figure 4:
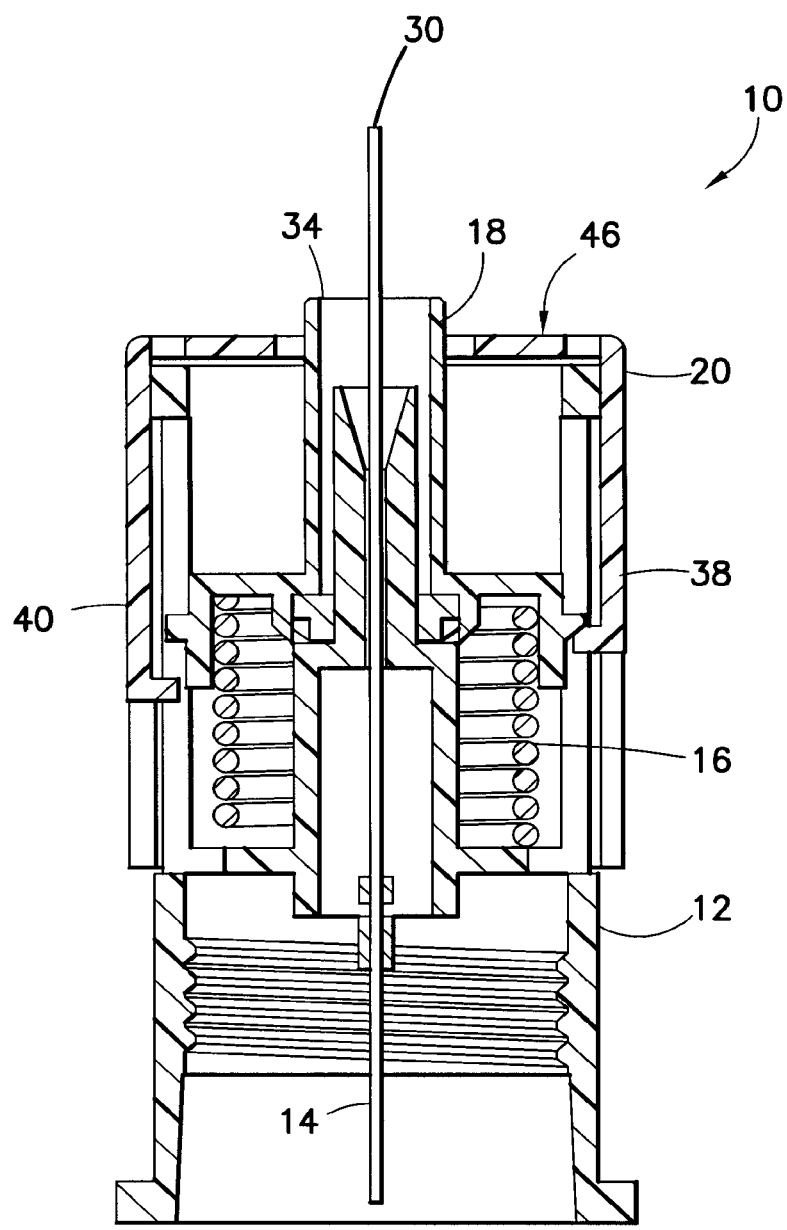
Figure 5:
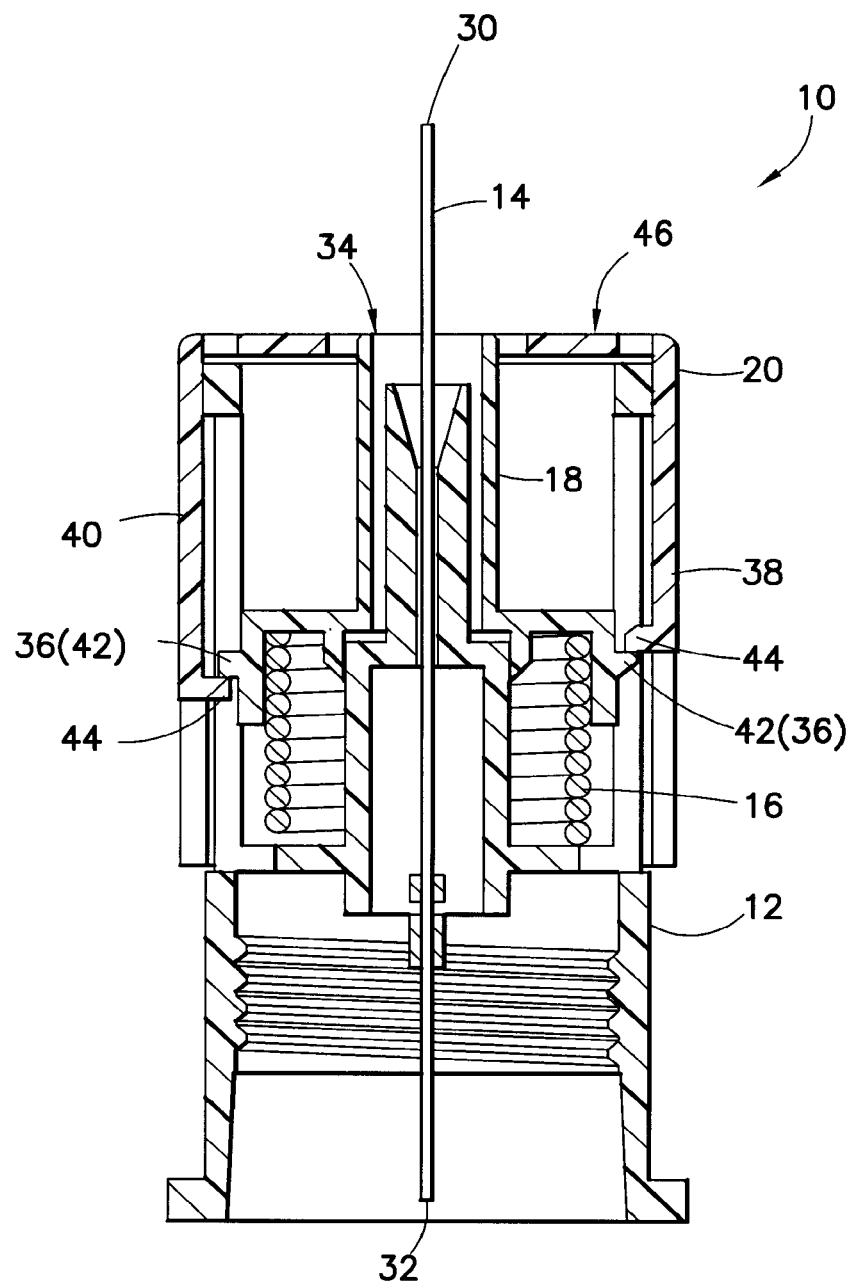

With reference to FIGS. 3-5, during an injection procedure, the skin engaging surface 34 presses against a patient's skin, and the first shield 18 is urged proximally against the spring 16. It is preferred that the first shield 18 and the second shield 20 be formed with cooperating elements to allow for locking interengagement therebetween upon sufficient proximal movement of the first shield 18. Specifically, as shown in FIG. 5, the second shield 20 may be formed with at least one first locking arm 38 and at least one second locking arm 40, with the second locking arm 40 having a greater length than the first locking arm 38. One or more detents 42 may be provided on the first shield 18, and locking protrusions 44 may be formed on the first and second locking arms 38, 40. The projections 36 may additionally act as the detents 42, with only the projections 36 being provided. The detents 42 are caused to be interposed between the locking protrusions 44 upon sufficient proximal movement of the first shield 18. With this interposed state, as shown in FIG. 5, the first and second shields 18, 20 are locked together so as to permit movement in concert therebetween. The force of movement generated by the spring 16 is transmitted to the second shield 20 via the first shield 18 (the first shield 18 directly engaging the spring 16). With the configuration shown in the figures, the second shield 20 is releasably retained on the hub 12 by an interference fit, e.g., an interference fit between the inner diameter of the second shield 20 and the outer diameter of the hub 12.

The first shield 18, particularly the location of the skin engaging surface 34, the first and second locking arms 38, 40, the detents 42 and the locking protrusions 44 are shaped and located so that the first and second shields 18, 20 may be locked together with the skin engaging surface 34 not having to be pushed proximally into the assembly 10 further than distal face 46 of the second shield 20. Specifically, the skin engaging surface 34 should be required to be moved proximally to at most a generally coplanar position with the distal face 46, but not proximally of the distal face 46 of the second shield 20 to achieve a locked state between the first and second shields 18, 20.

With completion of an injection, the skin engaging surface 34 is removed from a patient's skin. The spring 16 then causes the first shield 18 to move distally. With the second shield 20 being locked to the first shield 18, the second shield 20 likewise moves distally. The force of the spring 16 must be sufficient to overcome any retention force applied by a releasable retention arrangement, such as the interference fit. With reference to FIG. 1, the second shield 20 is urged distally to a shielding position in which the second shield 20 covers the distal end 30 of the needle 14.

Figure 6:
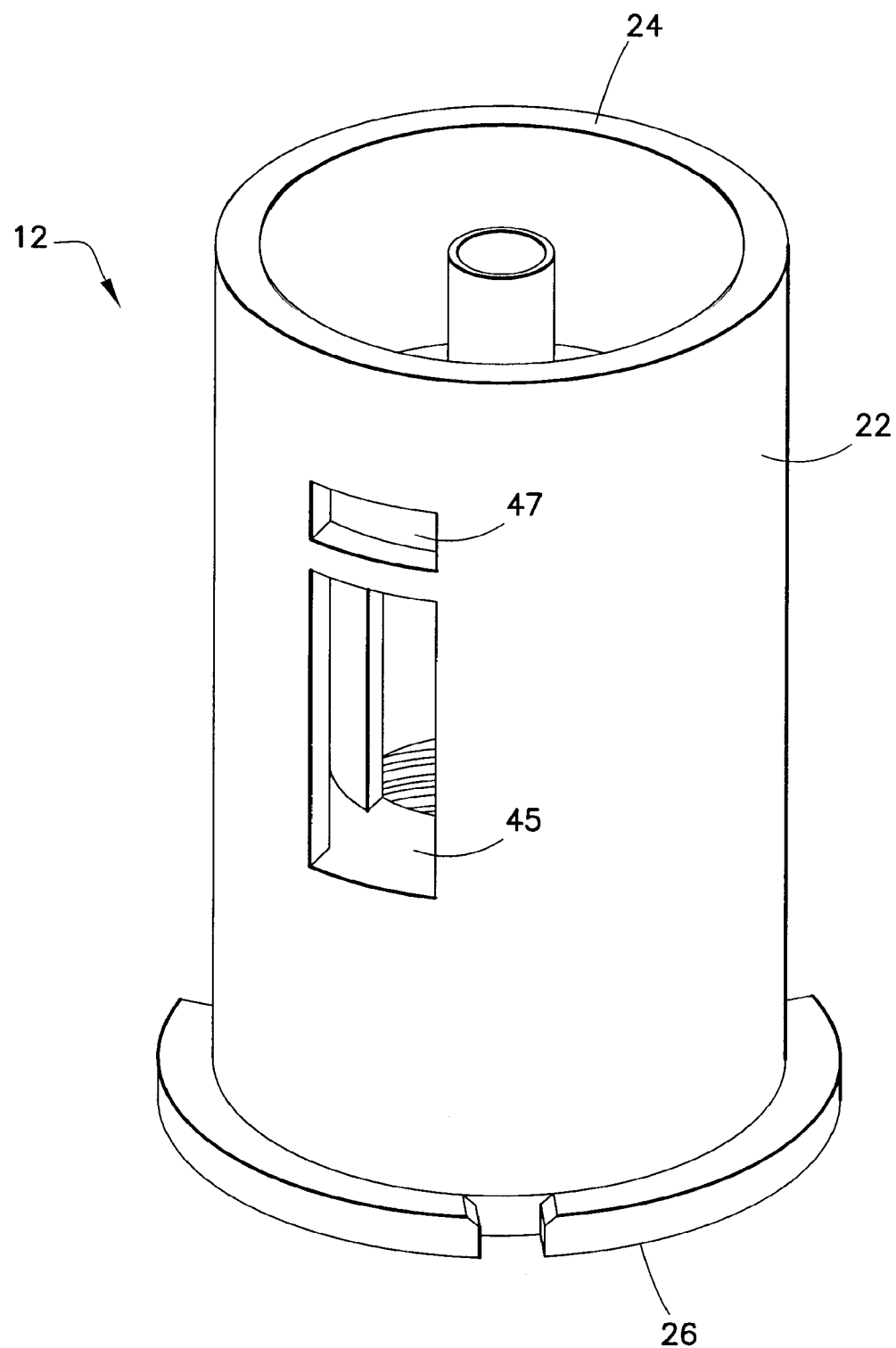
Figure 9:
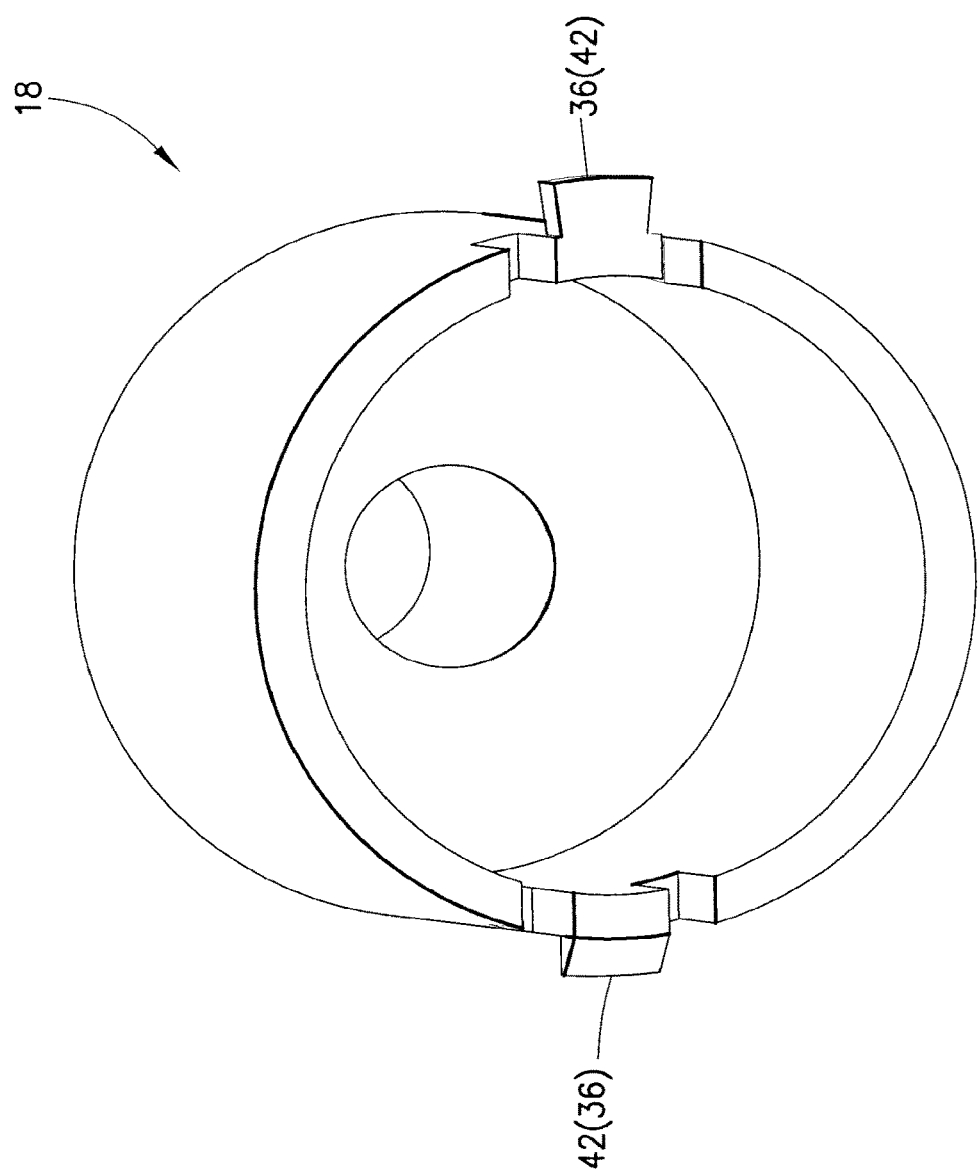
Figure 11:
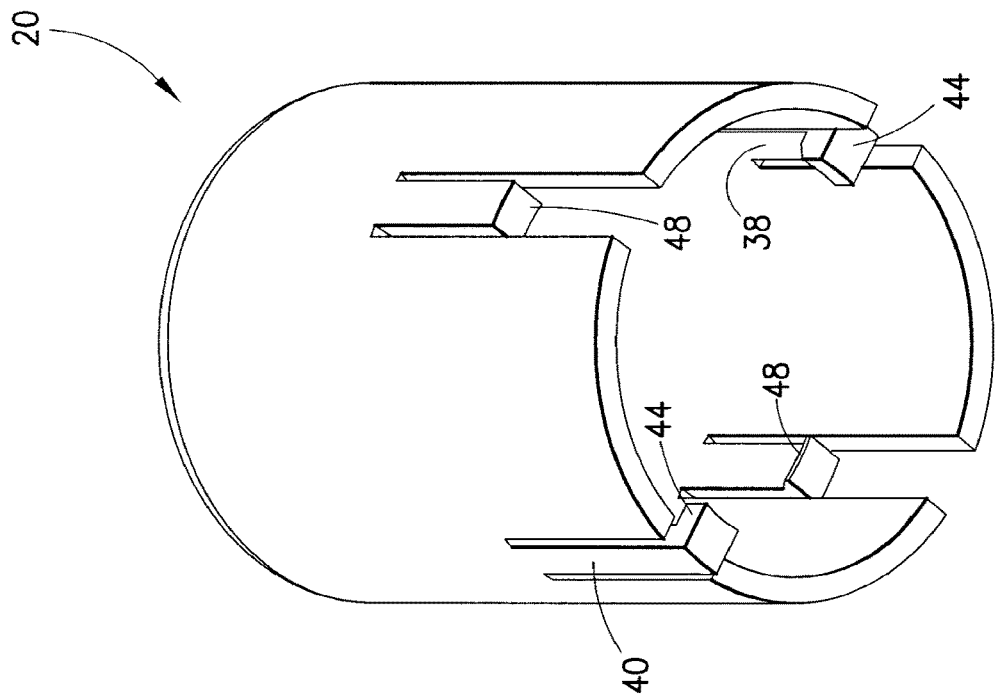
Figure 10:
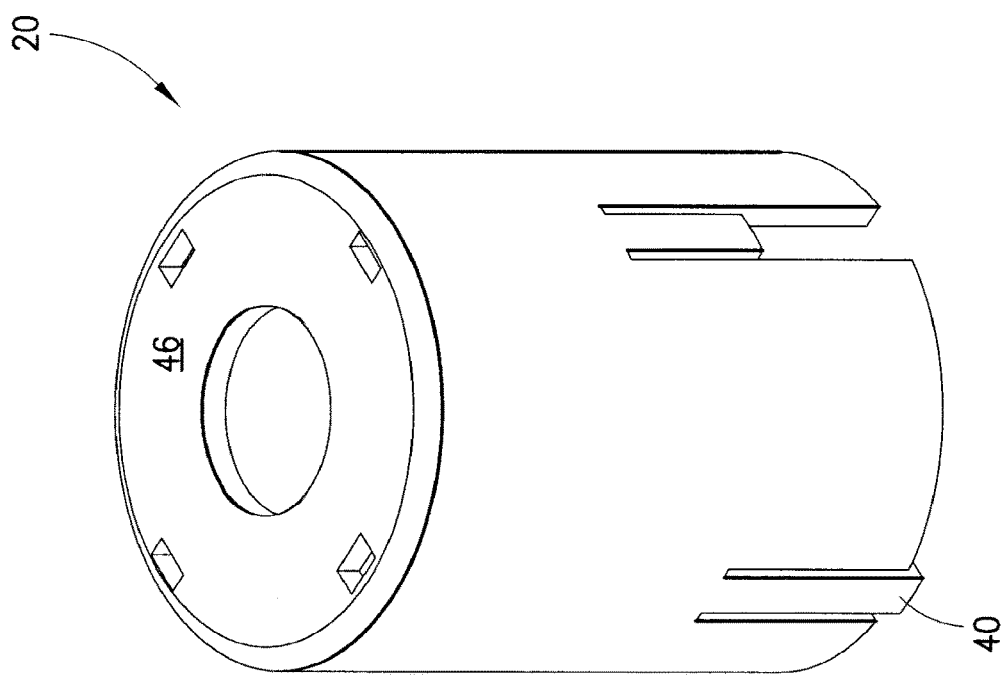

With reference to FIG. 11, one or more locking tabs 48 may be provided on the second shield 20 to engage corresponding features on the hub 12 and cause the second shield 20 to be locked in the shielding position. The locking tabs 48 may slide along guide channels 45 formed in the hub 12. The locking tabs 48 may come into snap engagement with the ends of the guide channels 45 or into snap engagement with locking apertures 47 formed adjacent to the guide channels 45 (FIG. 6). The first shield 18 may also be positioned in a shielding position to cover the distal end 30 of the needle 20 (FIG. 1).

Figure 12:
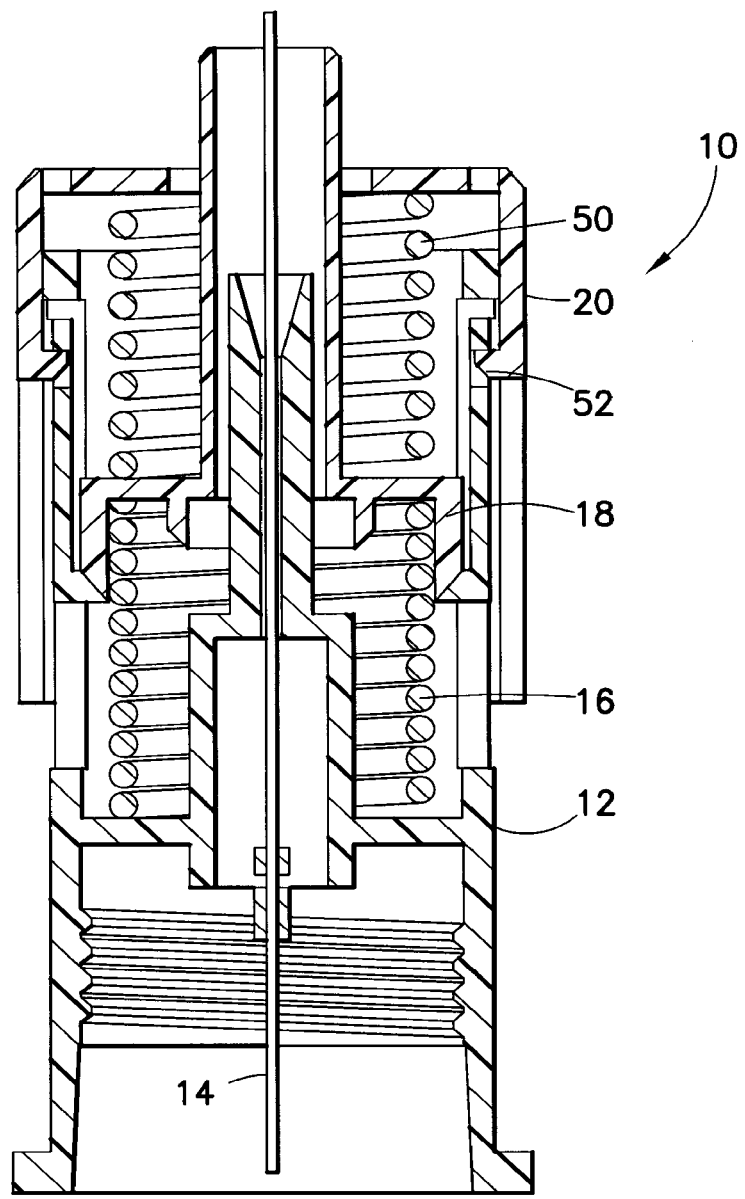
FIGS. 12-14 depict a variation of the first embodiment.
Figure 13:
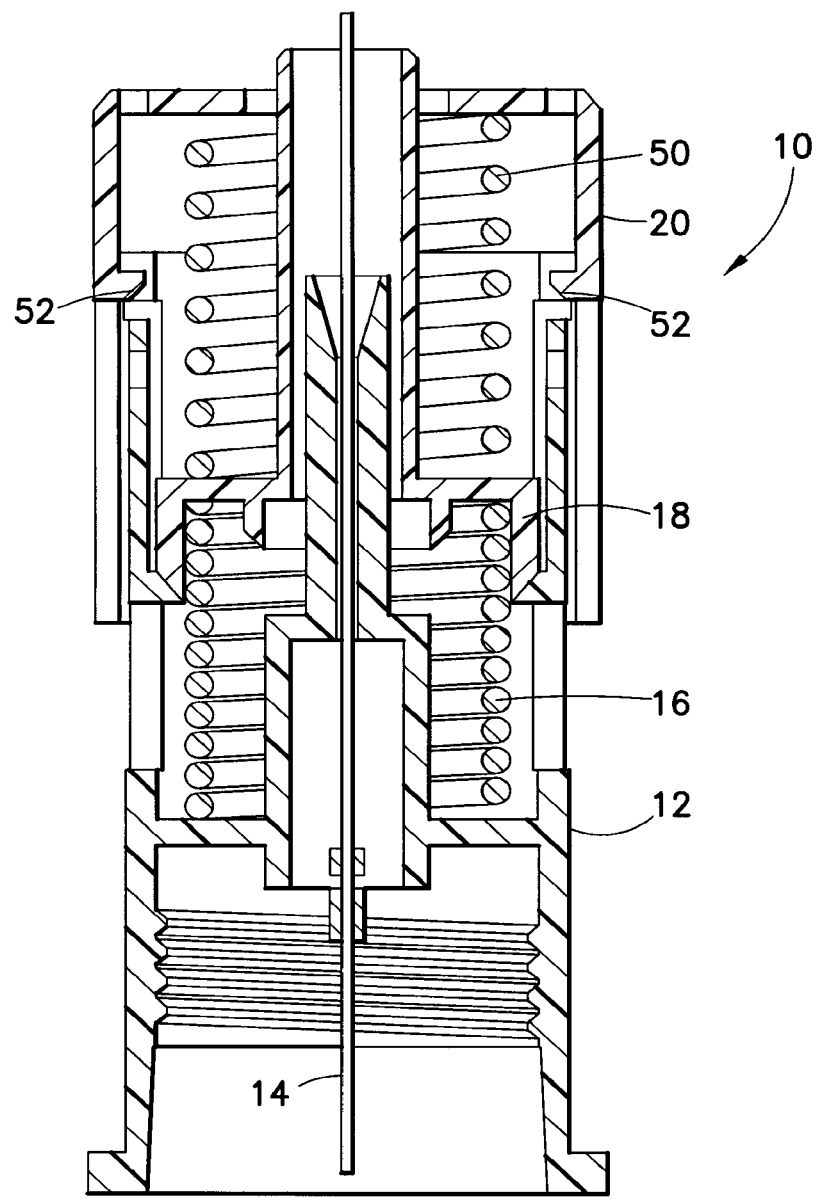
Figure 14:
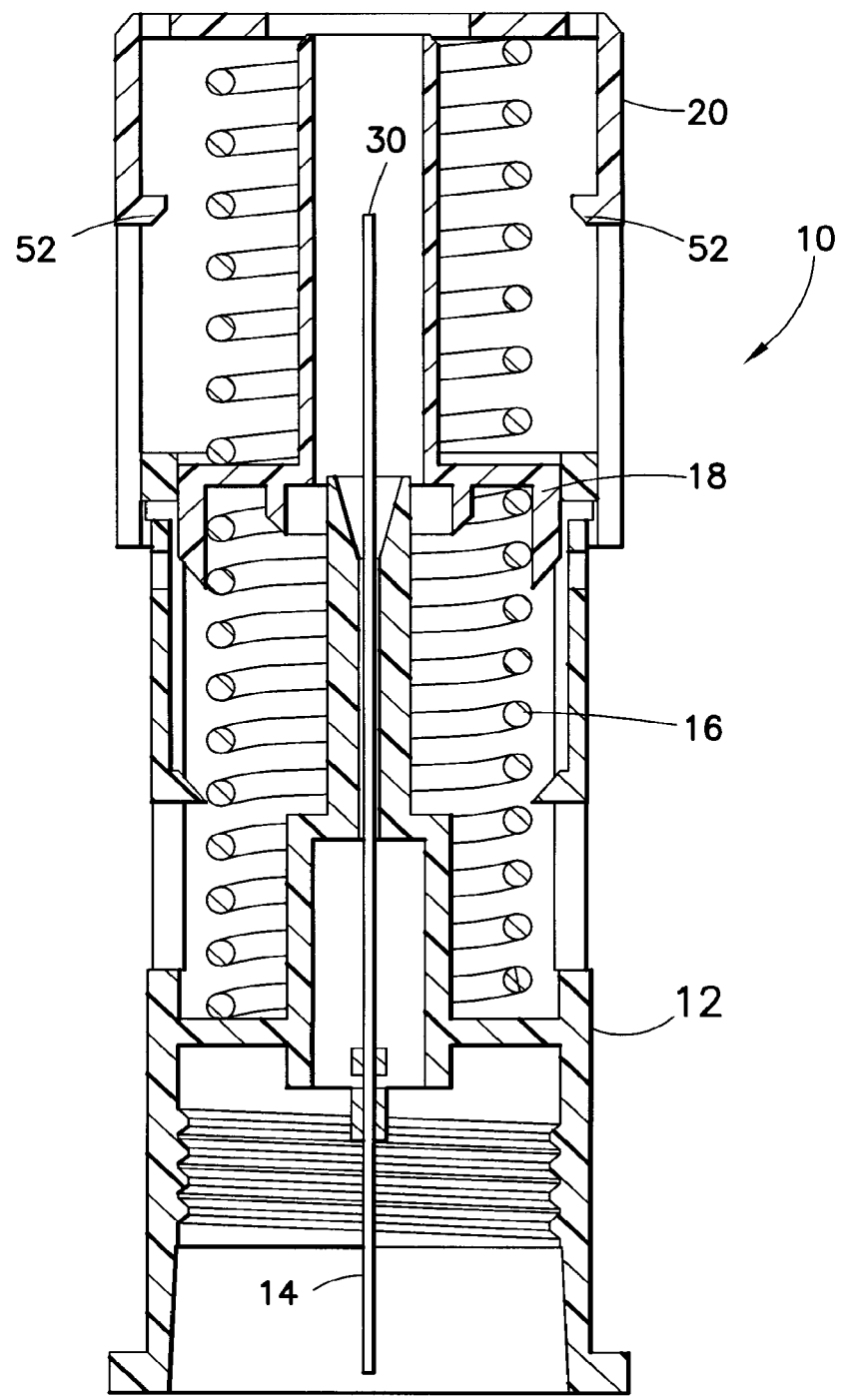

With reference to FIGS. 12-14 in a variation of the first embodiment, a secondary spring 50 may be additionally provided located between the first and second shields 18, 20. With this arrangement, the releasable retaining configuration discussed above with reference to the second shield 20 must provide sufficient retaining force against the secondary spring 50 to maintain the second shield 20 in the initial position prior to activation (e.g., the interference fit must provide greater retaining force than the force of movement generated by the secondary spring 50). In addition, the spring 16 should provide a greater spring force than the secondary spring 50. In this manner, the first shield 18 will overall experience a spring force urging the first shield 18 distally. An overall proximally-directed spring force may cause the first shield 18 to move proximally and activate prematurely. It is noted that a locking arrangement between the first and second shields 18, 20 is not necessary.

A releasable arrangement, such as with deflectable tabs 52 sitting in the guide channels 45, may be utilized where sufficient proximal movement of the first shield 18 results in outward deflection of the tabs 52 and release of the second shield 20. In an initial state, the tabs 52 engage the ends of the guide channels 45. Upon sufficient proximal movement of the first shield 18, the first shield 18 is configured to engage the tabs 52 and, thus, causing outward deflection thereof and release of the second shield 20. This may be preferable where the secondary spring 50 is utilized.

As shown in FIGS. 12-15, upon activation of the assembly, both the spring 16 and the secondary spring 50 extend and provide a force of movement to the second shield 20. In a shielding position, the second shield 20 may be locked, as discussed above. The first shield 18 need not be locked and may be retained wholly within the assembly 10 between the spring 16 and the secondary spring 50.

In a second embodiment, as indicated above, the second shield 20 may act as a trigger for activating the assembly 10. With reference to FIGS. 15-26, the second shield 20 in this embodiment is located to be in an initial position extending distally from the hub 12 in a similar manner to that described above with respect to the initial position of the first shield 18. In addition, the first shield 18 is provided with a releasable retaining arrangement to maintain the first shield 18 in a first, initial position in which the first shield 18 does not cover the distal end 30 of the needle 14. For example, with reference to FIG. 18, one or more deflectable fingers 54 may be provided on the hub 12 to interferingly engage with the first shield 18 to restrict distal movement thereof. The releasable retaining arrangement should provide sufficient retaining force to hold the first shield 18 in the initial position against the force of the spring 16.

Figure 16:
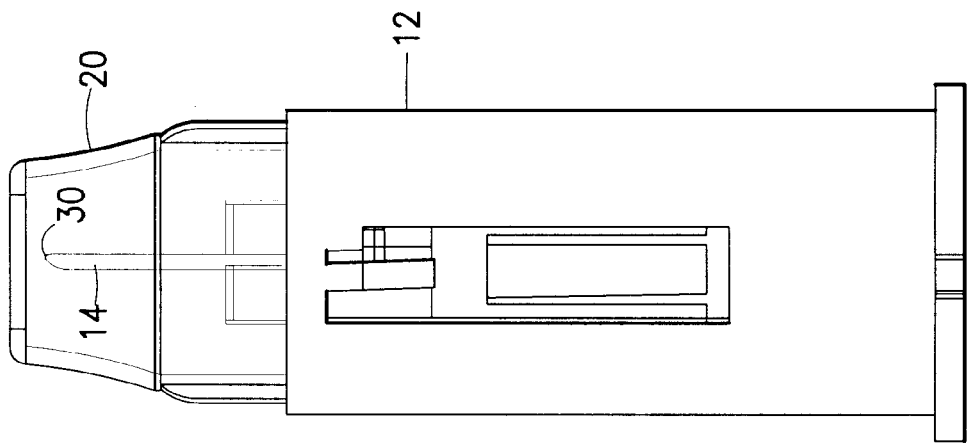
Figure 15:
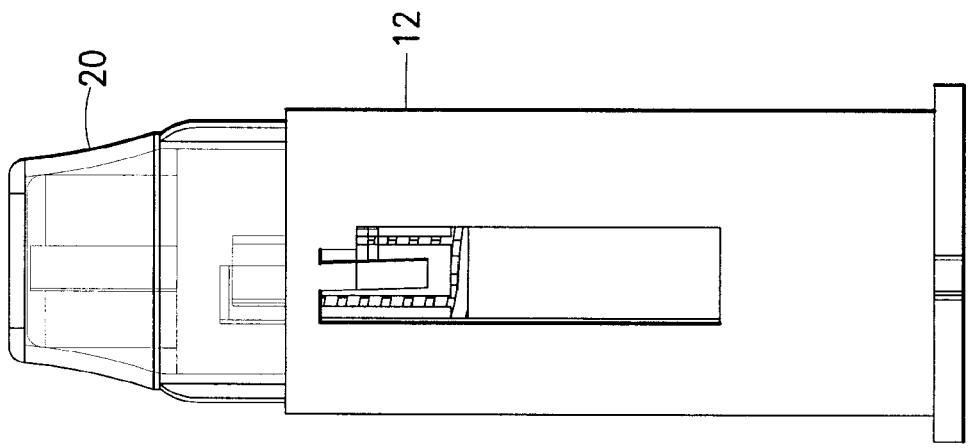
Figure 18:
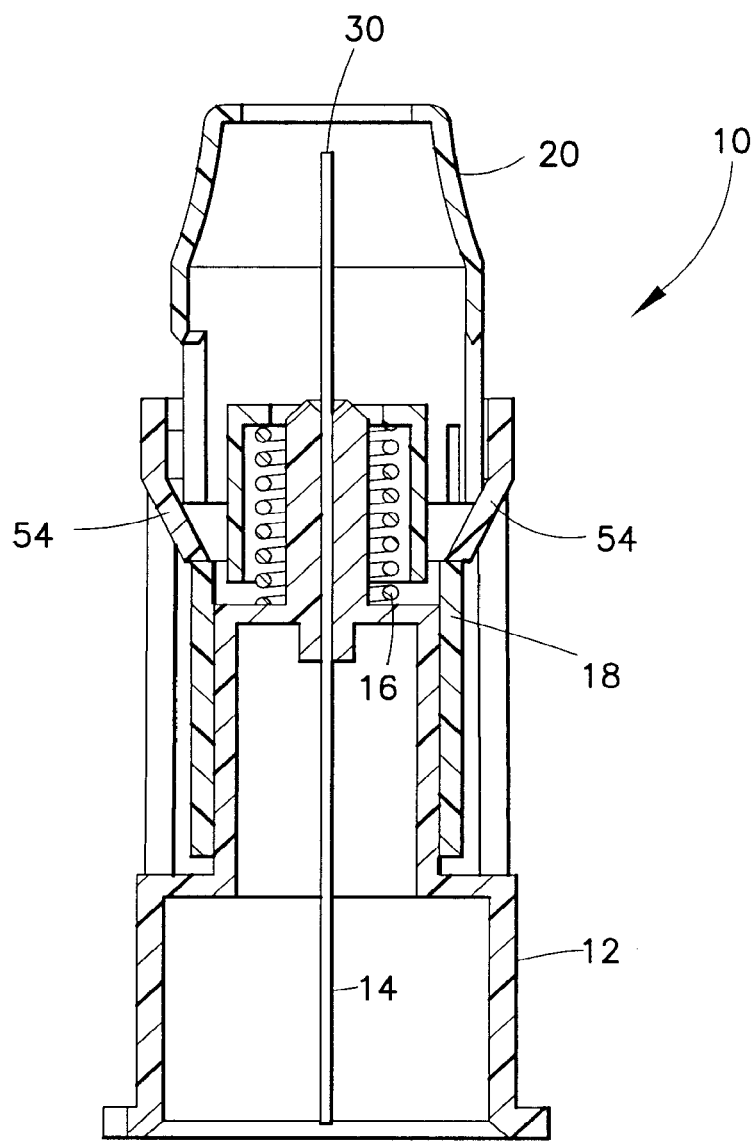
Figure 19:
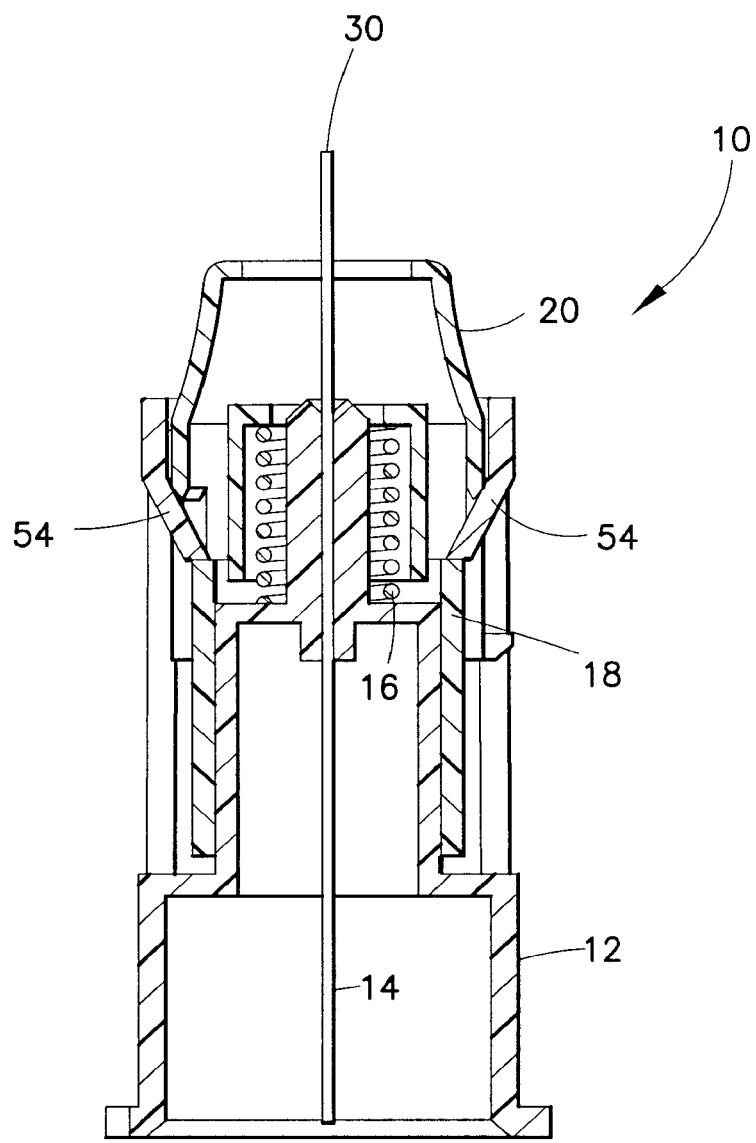
Figure 20:
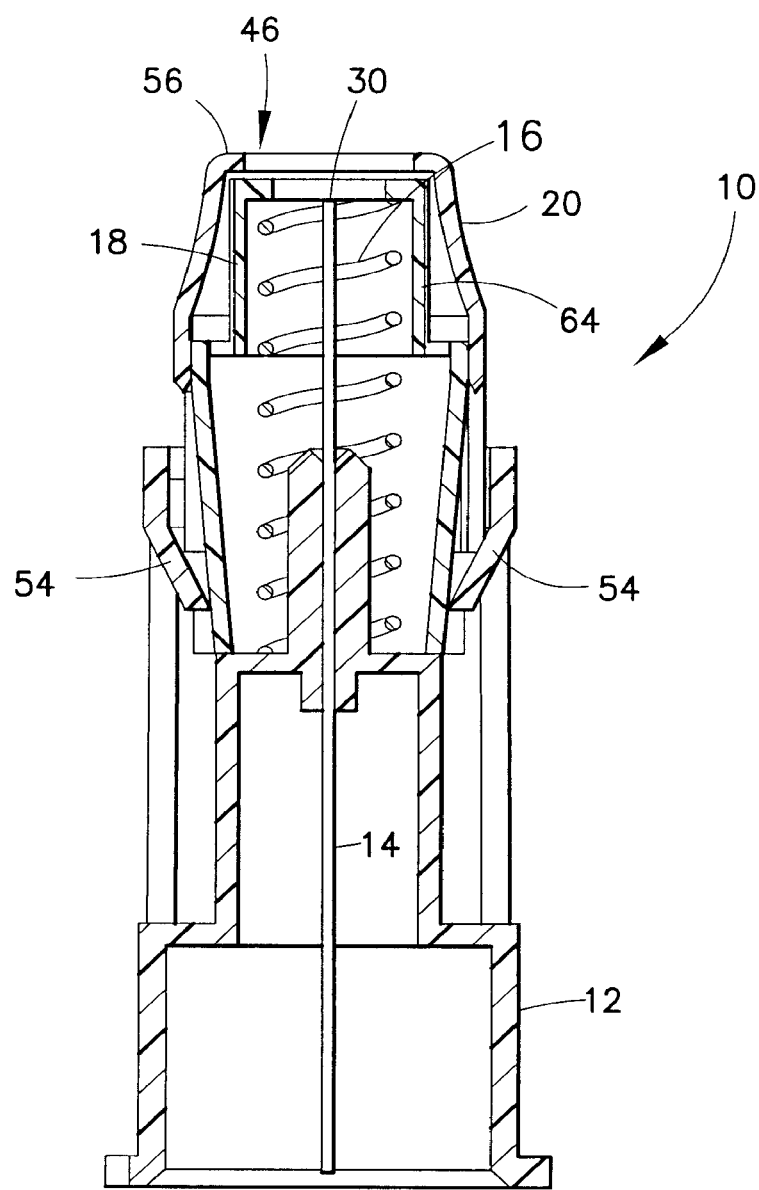
Figure 22:
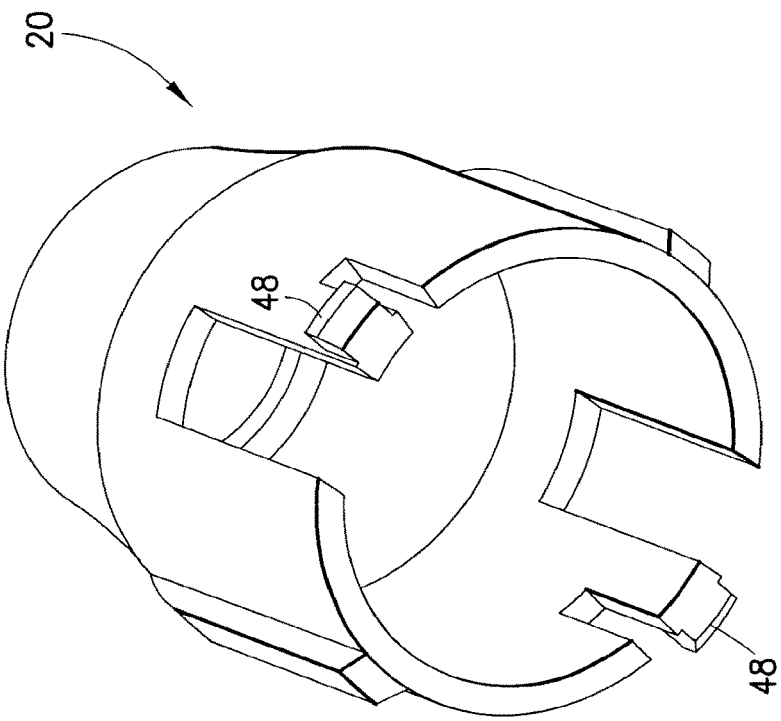

With the second embodiment, the skin engaging surface 34 is defined on the second shield 20. With sufficient proximal movement of the second shield 20 during an injection procedure, in a manner similar to that described above with respect to the first shield 18, the second shield 20 causes release of the releasable retaining arrangement and permits distal movement of the first shield 18 under force of the spring 16. For example, sufficient proximal movement of the second shield 20 may cause the second shield 20 to engage the fingers 54 and to cause outward displacement thereof into non-interfering positions. As best shown in FIGS. 16 and 20, the first shield 18 is urged distally under force of the spring 16 to a shielding position where the distal end 30 of the needle 14 is covered. A locking configuration, such as that described above, may be utilized to lock the second shield 20 to the first shield.

Figure 28:
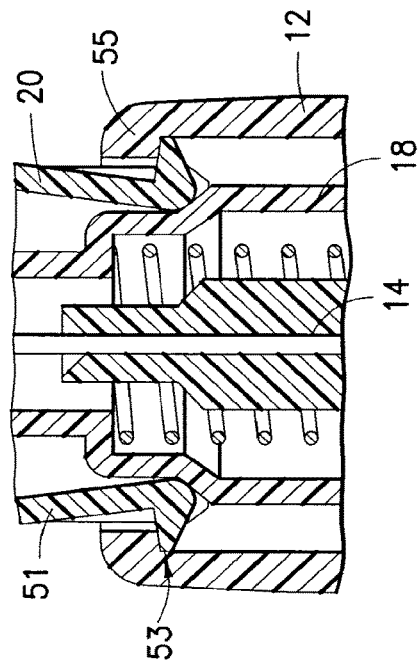
Figure 27:
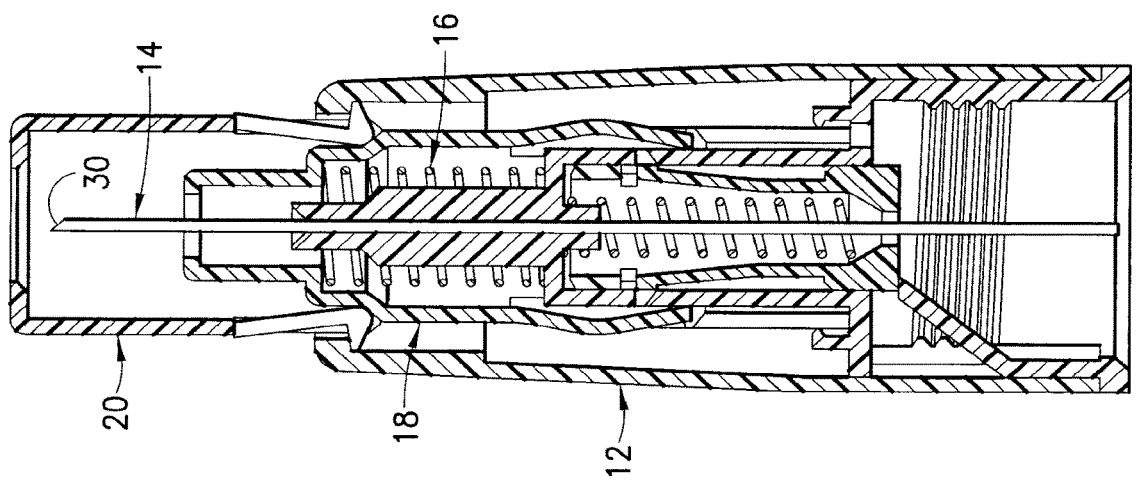
Figure 29:
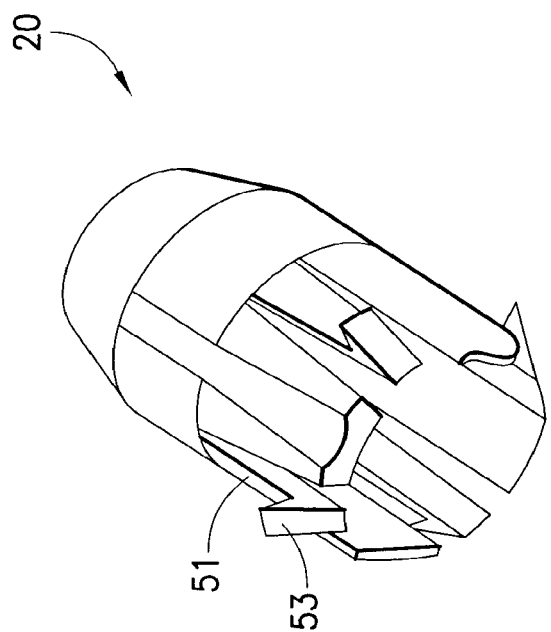

In a variation of the second embodiment, with reference to FIG. 27, in an initial, before use state, the second shield 20 covers the distal end 30 of the needle 14. As discussed above, in an initial state, the distal end 30 may be exposed for visual inspection. In addition, preferably, the first shield 18 does not cover the distal end 30 of the needle 14. A releasable retaining configuration is provided for releasably retaining the first shield 18 in the state shown in FIG. 27. The releasable retaining configuration may be provided with the second shield 20 having formed thereon at least one inwardly deflectable retaining arm 51. In an initial, before use state, the one or more retaining arms 51 are inwardly deflected, as shown in FIG. 27, to interferingly engage the first shield 18 so as to prevent distal movement of the first shield 18 under force of movement of the spring 16. The inward deflection of the retaining arms 51 may be caused by engagement with the surrounding portion of the hub 12. The hub 12 may be configured (e.g., radially sized) to cause the inward deflection of the retaining arms 51. Optionally, the retaining arm(s) 51 may each be provided with a hook 53 for engaging inwardly-extending lip 55 formed on the hub 12 (FIGS. 28 and 29). The interengagement of the hooks 53 and the lip 55 prevents the first shield 16 from coming out of the hub 12 before use under force from the spring 16.

Figure 31:
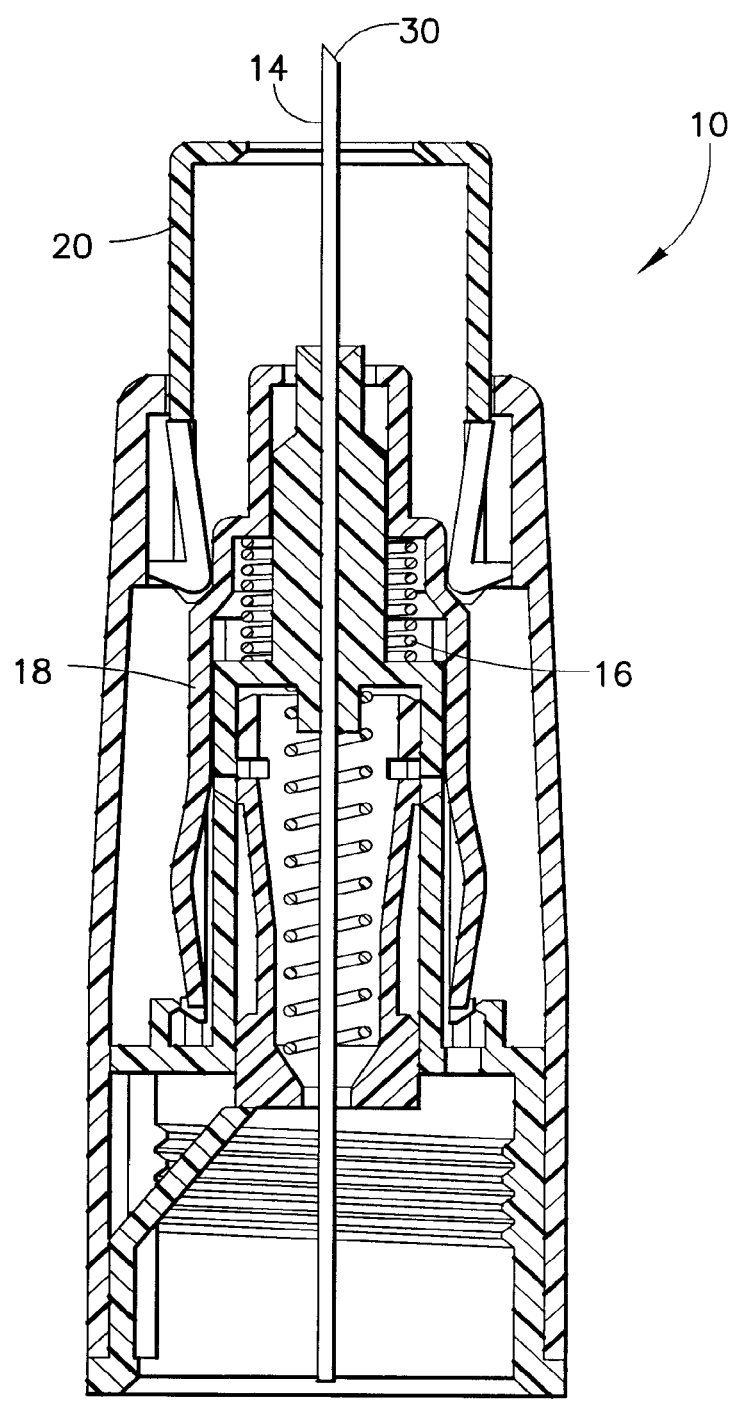

With reference to FIGS. 31-36, use of the assembly 10 is shown. FIG. 31 shows the second shield 20 having been moved proximally from the initial, before use state shown in FIG. 27. Proximal movement is achieved with the second shield 20 being pressed against a patient's skin and further pressure being applied causing the second shield 20 to move proximally relative to the rest of the assembly 10.

Figure 32:
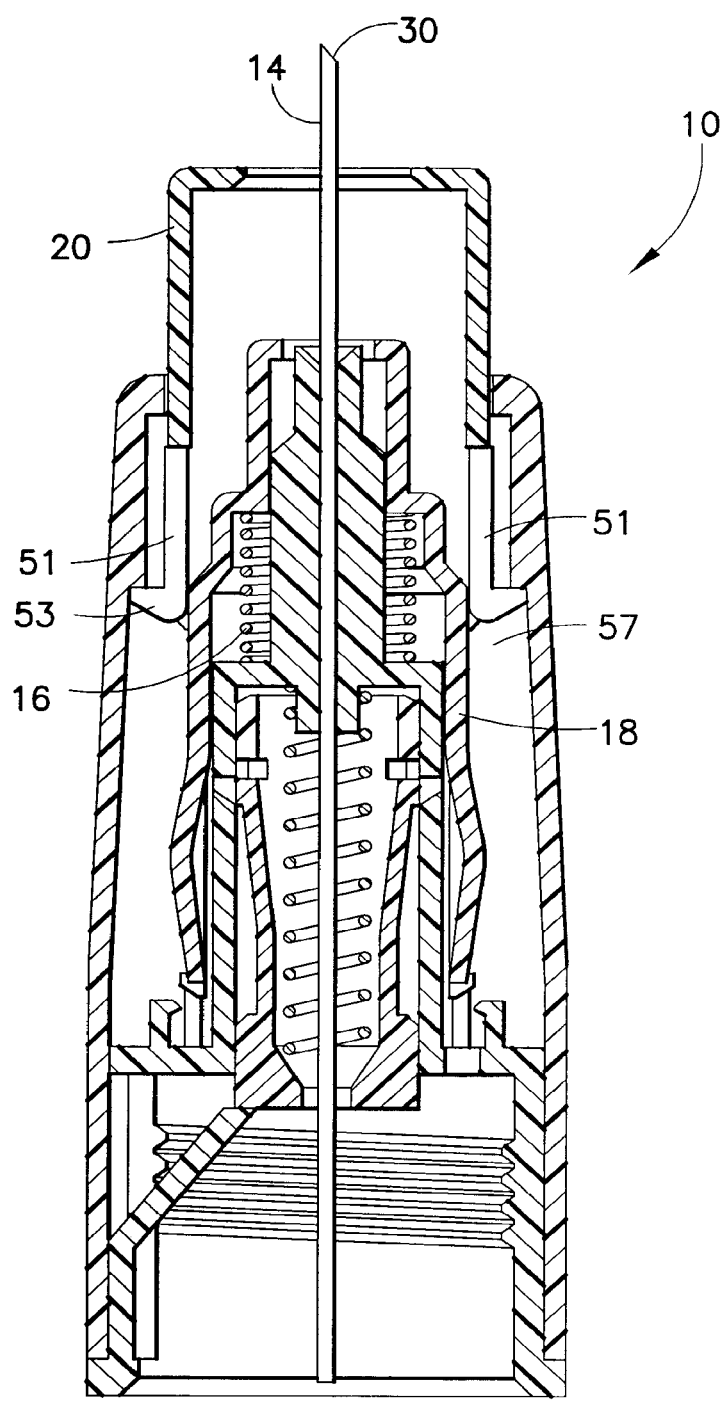
Figure 33:
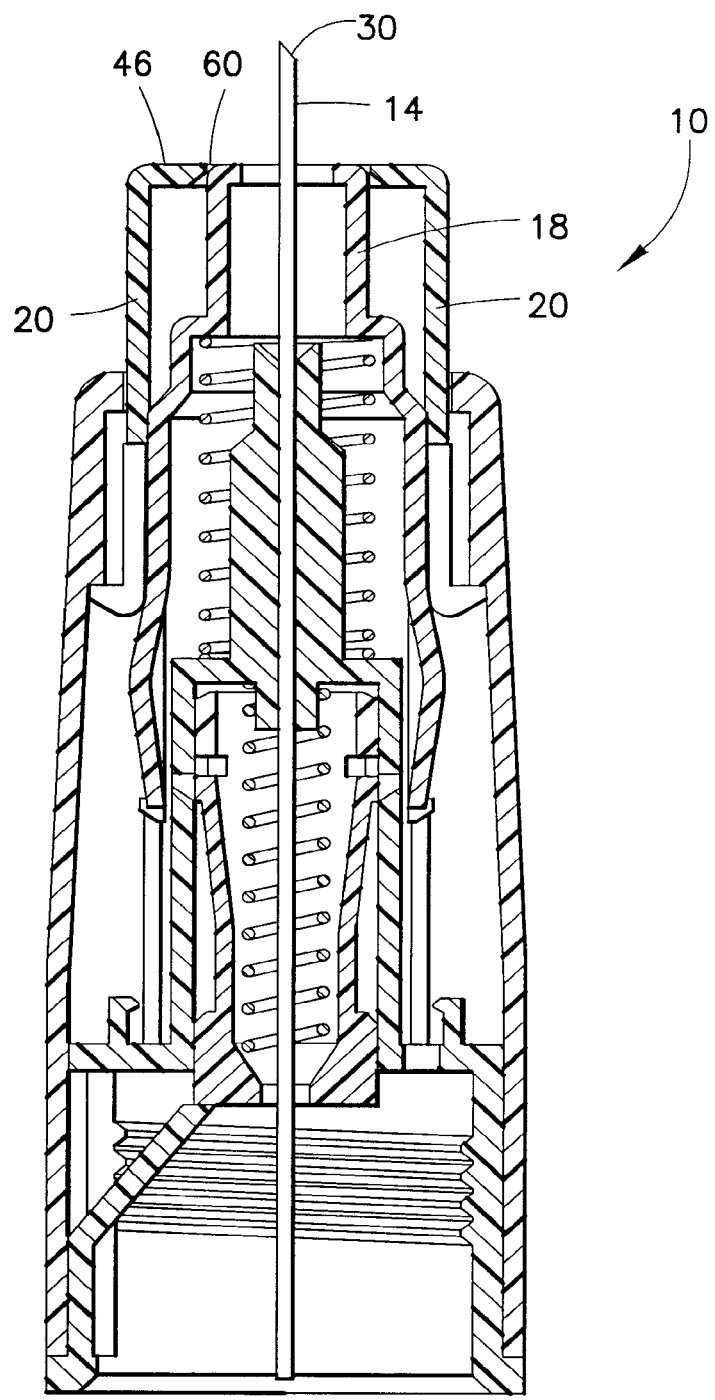
Figure 34:
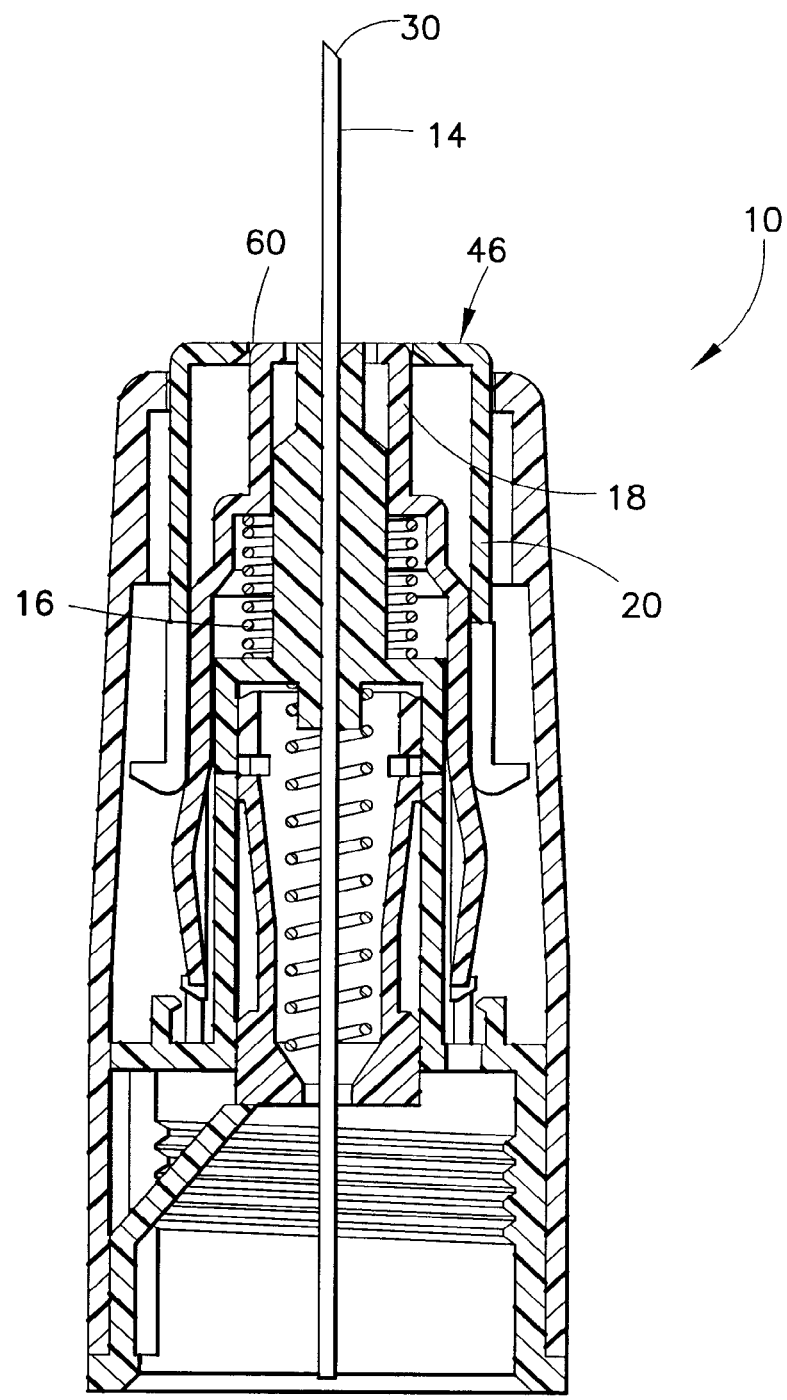
Figure 35:
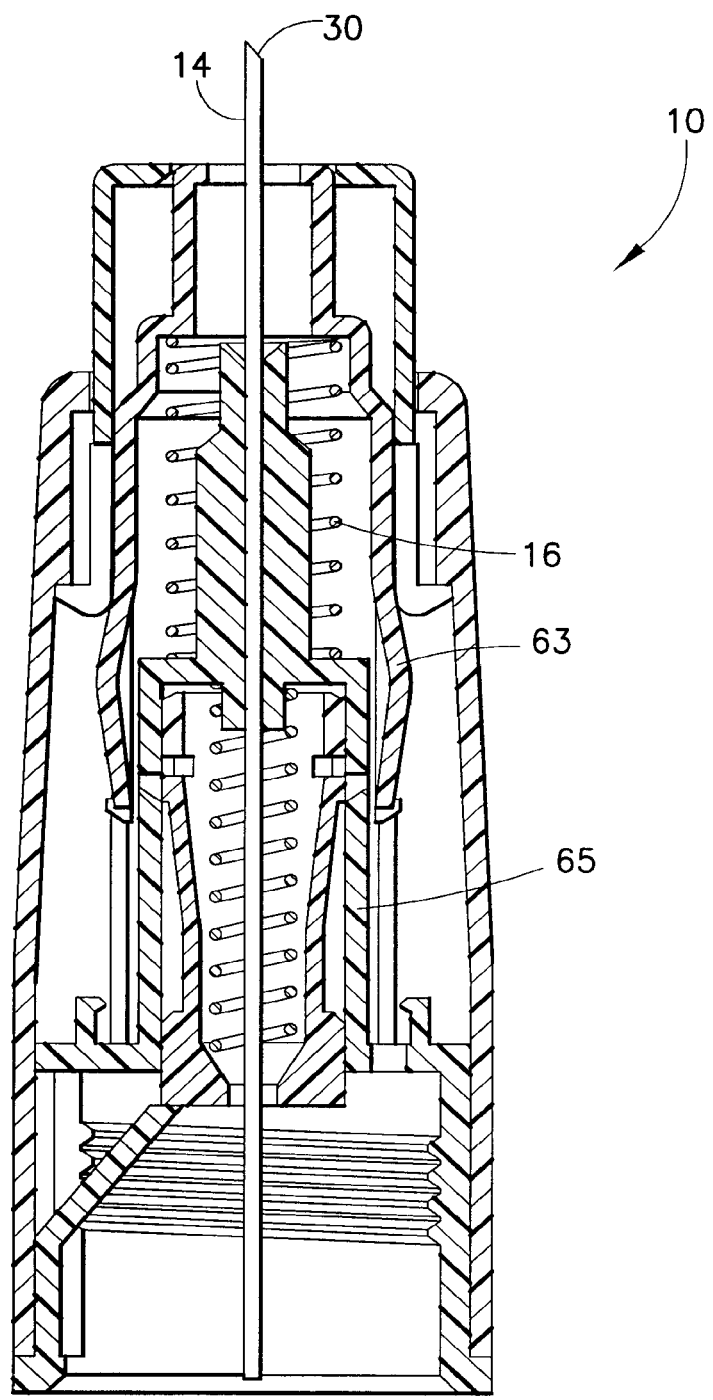
Figure 36:
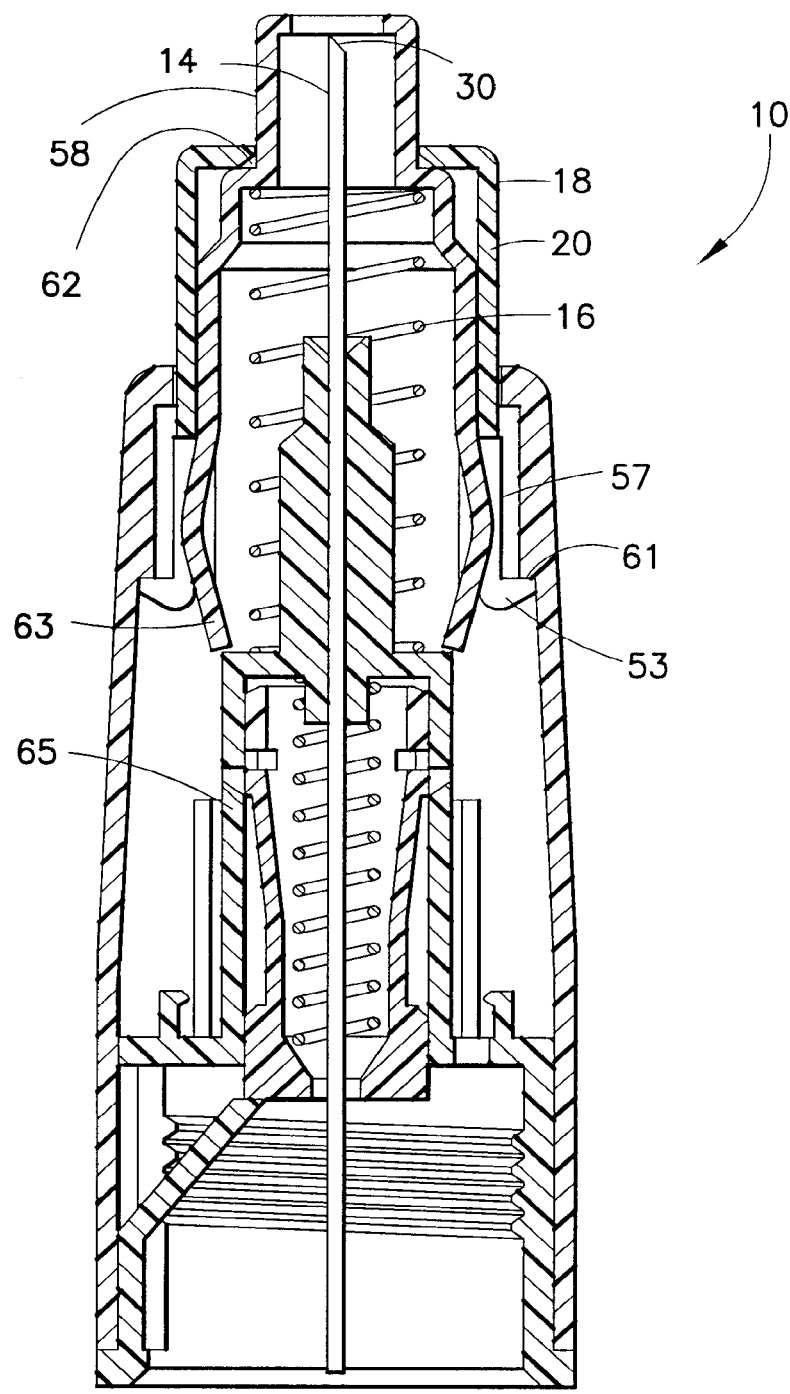

In the state shown in FIG. 31, the one or more retaining arms 51 still interferingly engage the first shield 18. With sufficient extent of proximal movement of the second shield 20, as shown in FIG. 32, the retaining arms 51 deflect outwardly to no longer prevent distal movement of the first shield 18. Enlarged area 57 may be provided in the hub 12 for permitting the retaining arms 51 to deflect outwardly, particularly the hooks 53. With no interference from the retaining arms 51, and with reference to FIG. 33, the spring 16 causes the first shield 18 to move distally. The first shield 18 moves to the state shown in FIG. 33 where the first shield 18 and the second shield 20 are pressed against a patient's skin. An opening 60 is formed through the distal end 46 of the second shield 20 to permit at least a portion of the first shield 18 to pass therethrough. During injection, the patient's skin prevents the first shield 18 from passing through the opening 60. As shown in FIG. 34, with further pressure applied to the assembly 10, the first and second shields 18, 20 are urged further proximally to expose the needle 14 in conducting a full injection. With reference to FIGS. 35 and 36, after the injection and as the needle 14 is withdrawn from a patient, the spring 16 causes the first shield 18 to move distally. The first shield 18 moves to a shielding position where the distal end 30 of the needle 14 is covered.

Figure 30:
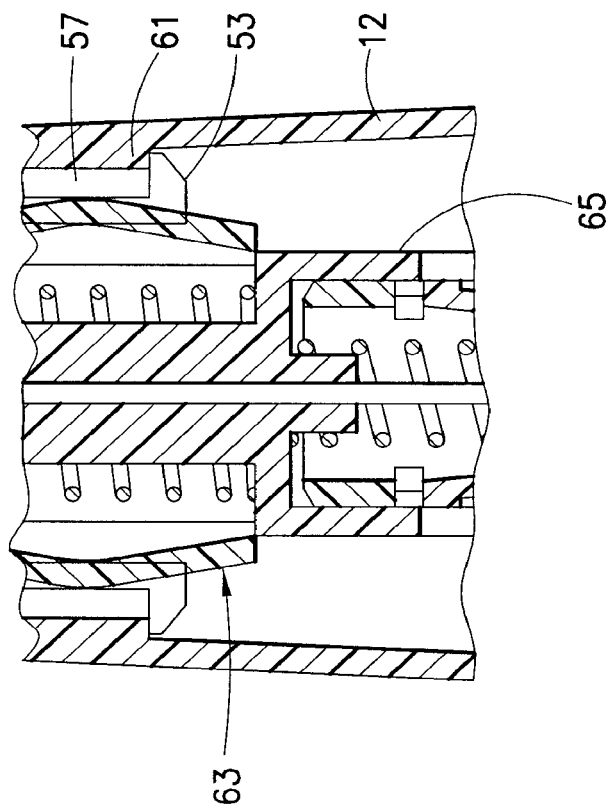

Distal movement of the first shield 18 may be limited by interengagement between the first and second shields 18, 20. In particular, the first shield 18 may be provided with a reduced diameter portion 58 sized to pass through the opening 60. A shoulder 62 formed on the first shield 18 may be formed with a larger diameter than the opening 60, thus limiting passage of the first shield 18 through the opening 60. As shown in FIG. 36, the interengagement between the second shield 20 and the shoulder 62 limits distal movement of the first shield 18. Further, a ridge 61 may be defined within the hub 12 (e.g. adjacent to the enlarged area 57) disposed to be engaged by the hooks 53 in a final after-use state (FIG. 30). The ridge 61 is distally spaced from the lip 55. The interengagement of the hooks 53 with the ridge 61 limits the distal movement of the second shield 18. This limited extent of distal movement of the second shield 20, in turn, causes limited distal movement of the first shield 18.

A locking arrangement may also be provided to limit proximal movement of the first shield 18 once in the final shielding position where the first shield 18 covers the distal end 30 of the needle 14. To this end, and with reference to FIG. 30, the first shield 18 may be provided with at least one inwardly deflectable locking arm 63 which is formed to be biased against a sleeve portion 65 of the hub 12 prior to the final shielding position of the first shield 18. Upon sufficient distal movement of the first shield 18, as shown in FIG. 36, the locking arms 63 move clear of the sleeve portion 65 thereby permitting the locking arms 63 to deflect radially inwardly. The locking arms 63, deflected inwardly, interferingly engage a portion of the hub 12, particularly above the sleeve portion 65, so as to prevent proximal movement of the first shield 18. The locking arms 63 may also be formed to be curved or bent outwardly so as to engage the second shield 20 as the first shield 18 initially moves distally, as shown in FIGS. 34 and 35. This permits movement of the second shield 20 in concert with movement of the first shield 18, without the neck portion 58 coming out of the opening 60 (FIG. 35). The curved or bent locking arms 63 are flexed inwardly as the first shield 18 slides inside of the second shield 20. When the locking arms 63 move clear of the sleeve portion 65, the locking arms 63 deflect radially inwardly. The locking arms 63, deflected inwardly, interferingly engage a portion of the hub 12, particularly above the sleeve portion 65, so as to prevent proximal movement of the first shield 18 as shown in FIGS. 30 and 36.

In a further variation of the second embodiment, the releasable retaining arrangement may be defined by cooperating elements on the first and second shields 18 and 20 which cause relative movement between the first and second shields 18 and 20 with the first shield 18 being released. For example, with reference to FIGS. 37-42, the outer shield 20 may cause relative movement (e.g., rotation) between the first shield 18 and the second shield 20 thus causing the first shield 18 to move from a retained position to a second, free position where the first shield 18 may be urged distally.

Figure 37:
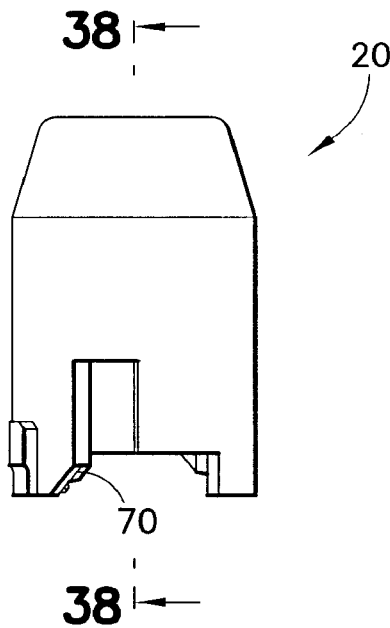
Figure 38:
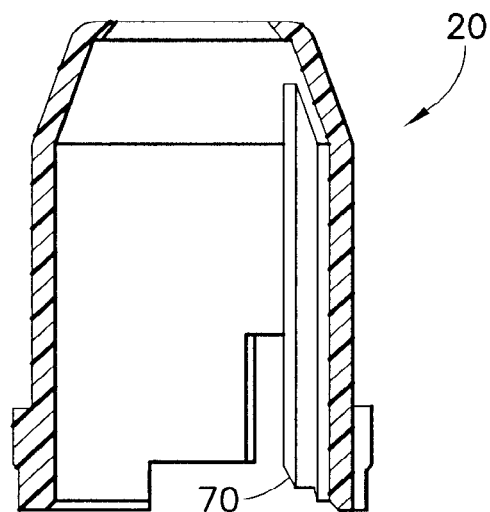
Figure 39:
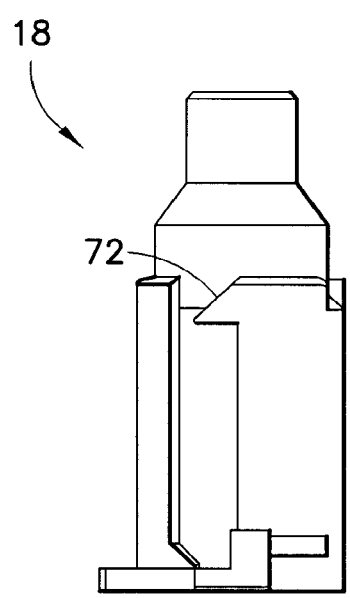

By way of non-limiting example, and with reference to FIGS. 37 and 38, the second shield 20 may include a protruding tapered surface 70. As shown in the figures, the tapered surface 70 may extend inwardly of the second shield 20, but may also extend outwardly. Correspondingly, a tapered receiving surface 72 may be formed on the first shield 72. The first and second shields 18, 20 are configured so that with the second shield 20 telescoped over the first shield 18, the tapered surface 70 will axially engage in abutting contact the receiving surface 72. Thus, in an initial state, the tapered surface 70 is aligned with the receiving surface 72. This interengagement retains the first shield 18 in an initial position against force of the spring 16.

Figure 40:
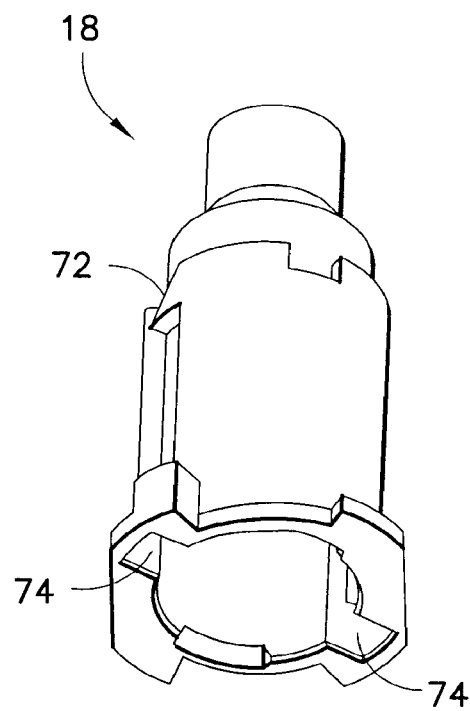
Figure 41:
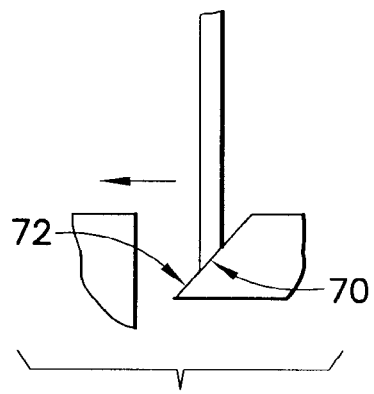
Figure 42:
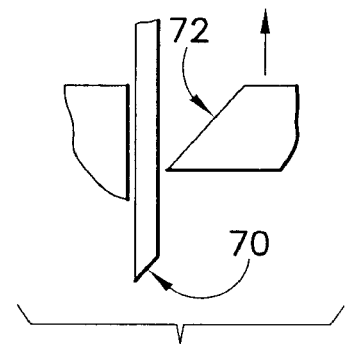

With proximal movement of the second shield 20 relative to the first shield 18, relative rotation between the first and second shields 18, 20 may be generated due to the tapered surfaces 70, 72 against each other under proximal movement. Preferably, the first shield 18 is non-rotatably held during the proximal movement of the second shield 20. With reference to FIG. 40, one or more lobes 74 may be formed on the first shield 18 for receiving portions of the hub 12. This interengagement limits rotation of the first shield 18 relative to the hub 12. With the first shield 18 being held in a fixed radial position, as shown in FIGS. 41 and 42, the tapered surface 70 may be caused to rotate out of engagement with the receiving surface 72. Once the receiving surface 72 is clear, the first shield 18 may be driven distally by the spring 16. As will be appreciated by those skilled in the art, the first shield 18 may be caused to move relatively to the second shield 20, vice versa, or the first and second shields 18, 20 may be both caused to move relatively. The relative movement may cause the first shield 18 to be freed of any retaining element, such element being formed on the second shield 20 and/or elsewhere (e.g., on the hub 12).

As will be appreciated by those skilled in the art, various releasable retaining arrangements are described above. It is to be understood that these arrangements may be used in various combinations and with any of the various embodiments. The releasable retaining arrangement may be defined by an interference fit; one or more movable elements defined on the hub; one or more movable elements defined on one of the shields (e.g., the second shield); and/or an arrangement defined between the shields wherein relative movement (e.g., radial movement) allows for release of the relevant shield.

Depending on the configuration of the first shield 18 and the second shield 20, the first shield 18 may engage the second shield 20 and transmit moving force to the second shield 20 to cause distal movement thereof. For example, with reference to FIG. 20, the second shield 20 is urged to a final position whereby the second shield 20 may cover all or part of the needle 14, including the distal end 30. In addition to, or as an alternative to, the locking arrangement provided on the first shield 18, a locking arrangement similar to that described above may be provided on the second shield 20 to lock the second shield 20 in its final position.

Figure 21:
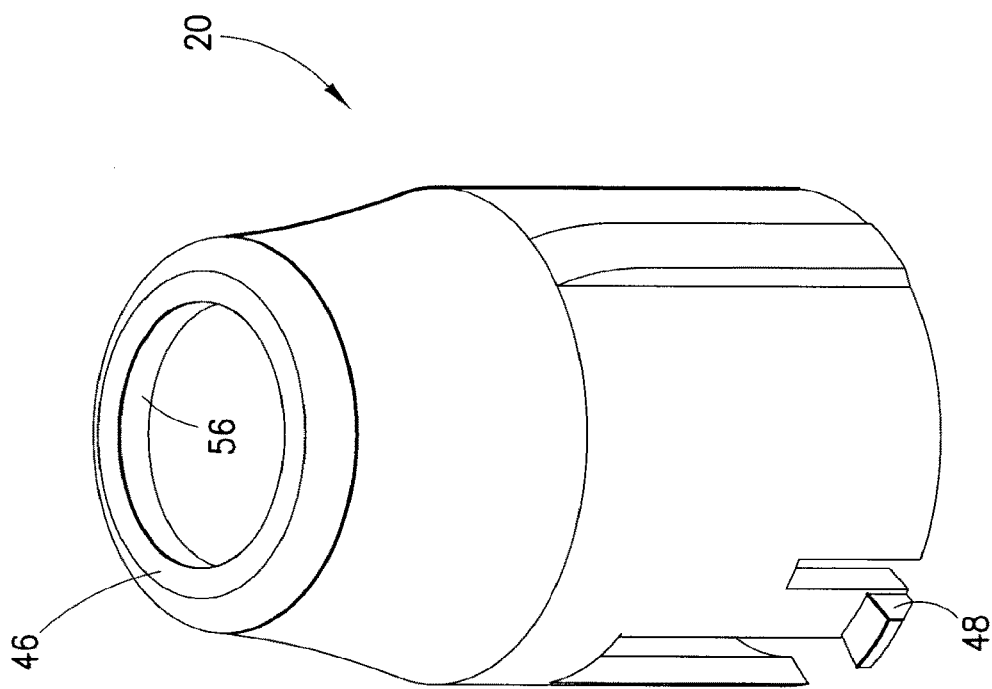
Figure 24:
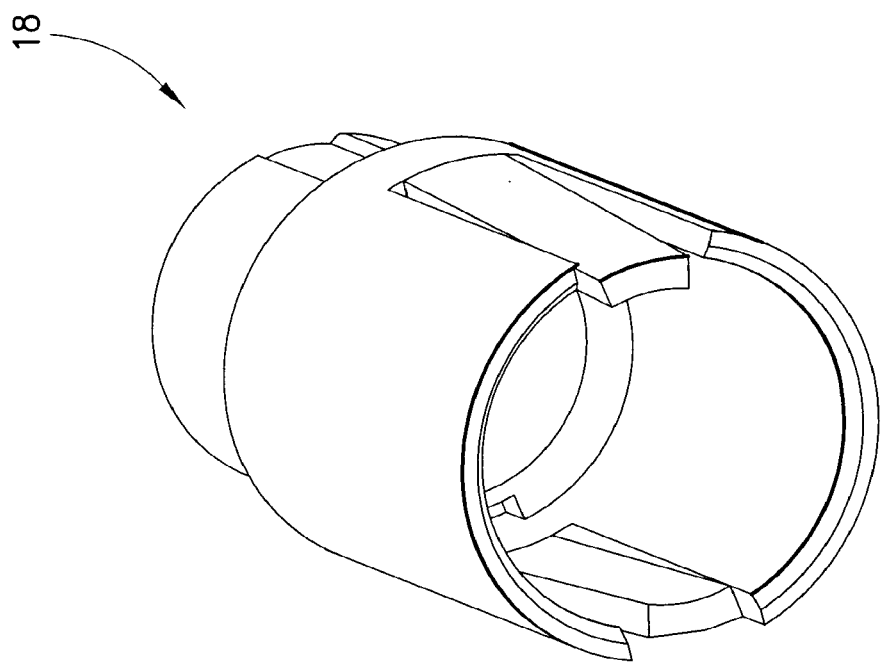
Figure 23:
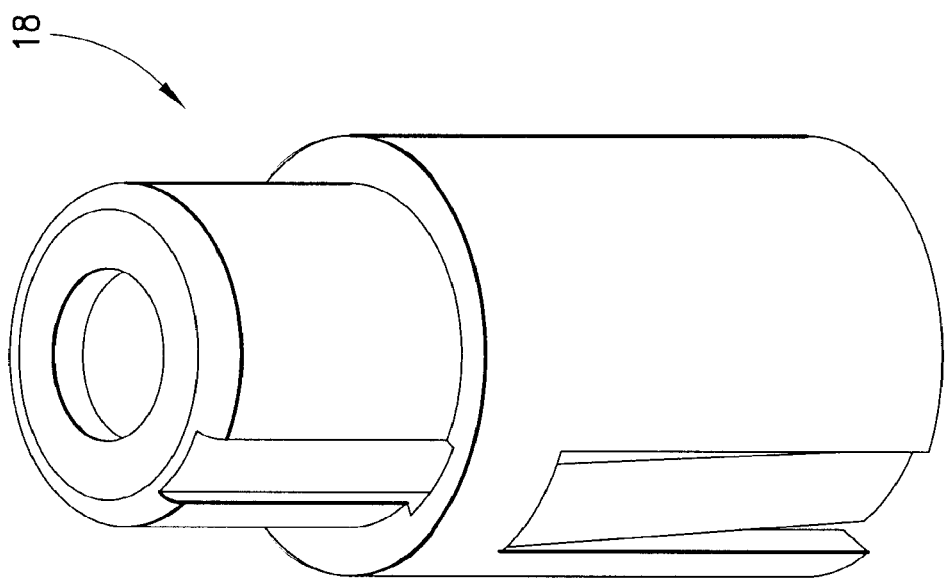
Figure 26:
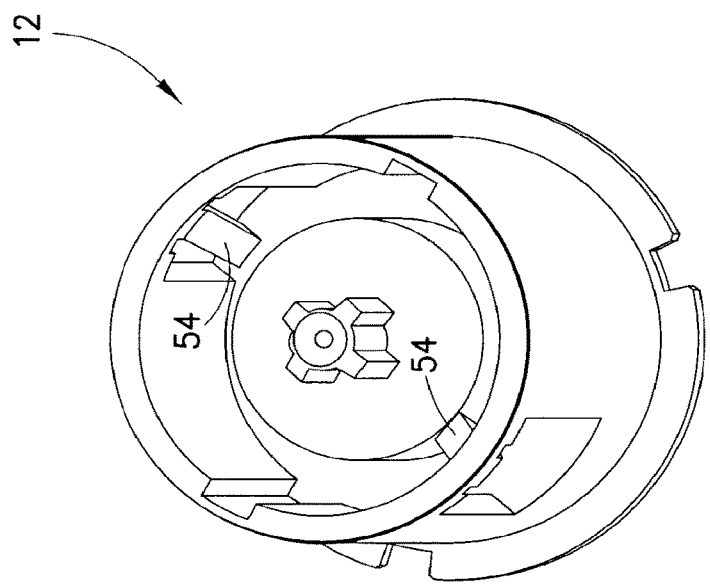
Figure 25:
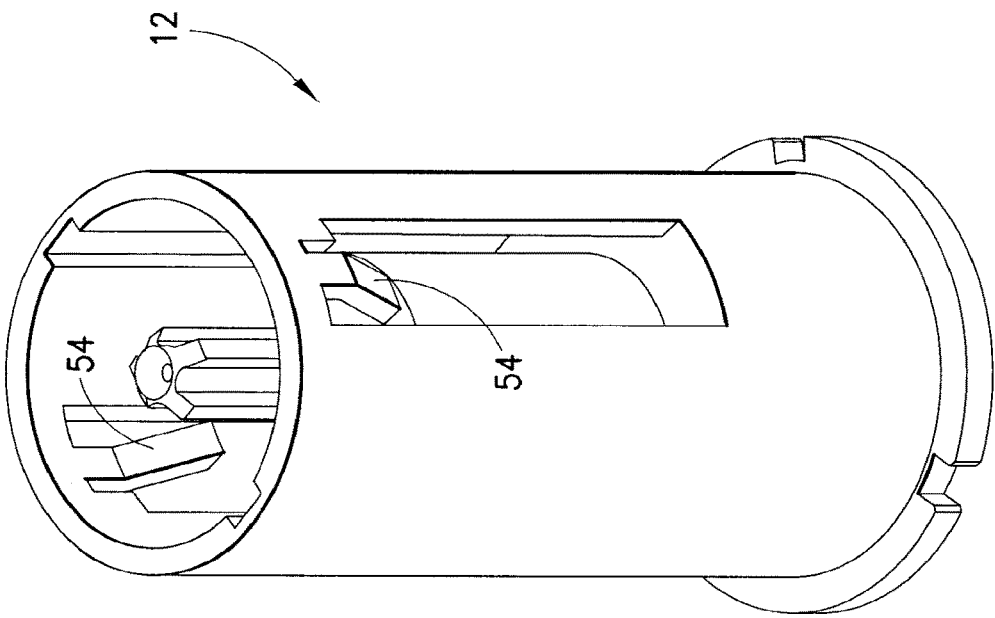
Figure 43:
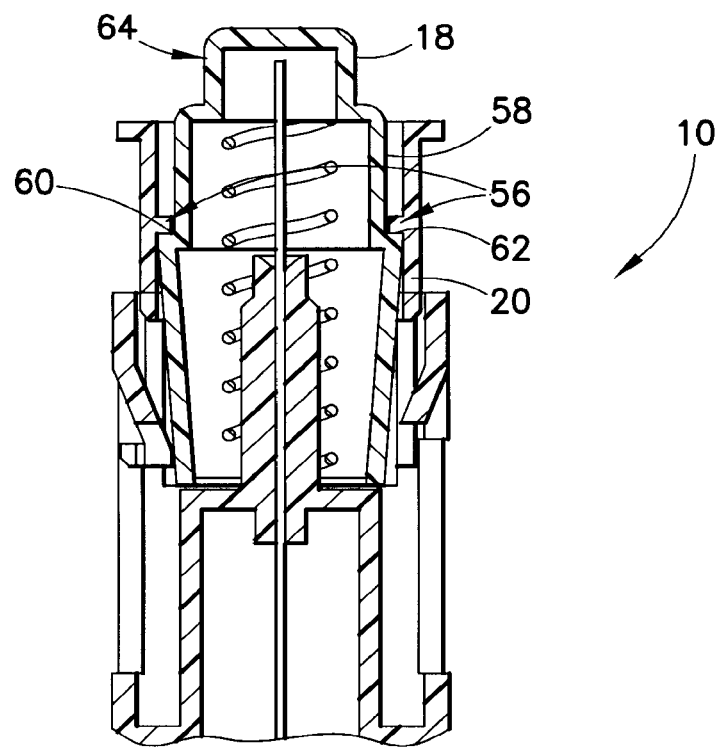
FIGS. 43-47 depict alternative configurations of the first and second shields useable with the subject invention; and,
FIGS. 48-50 depict before use, during use, and after use states, respectively, of the subject invention.
Figures 44, 45:
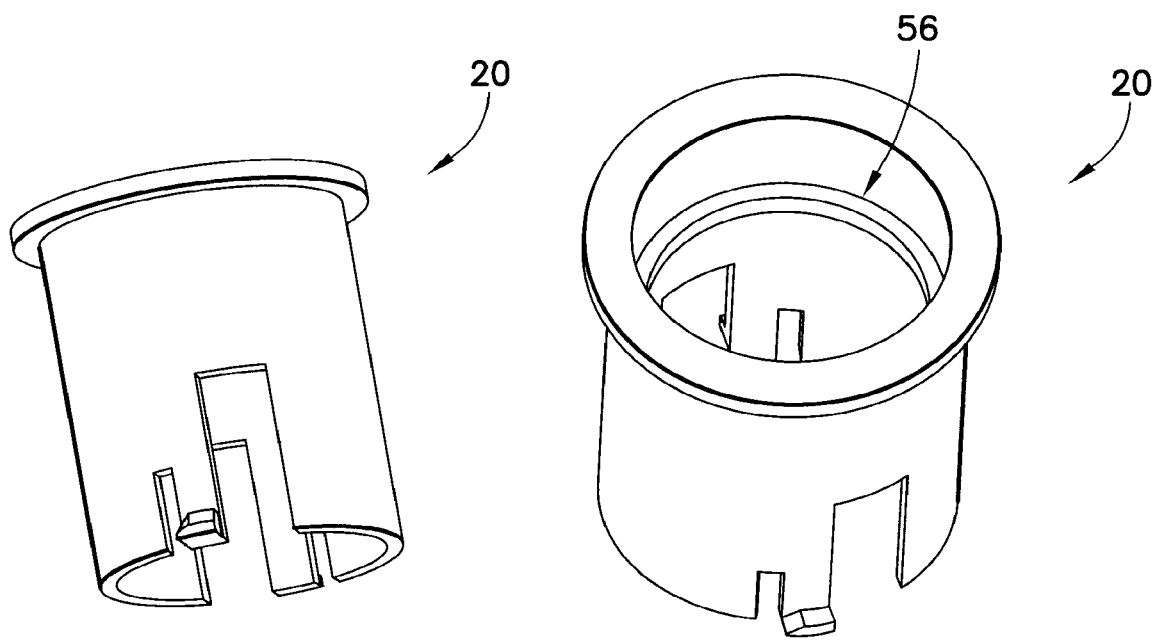
Figures 46, 47:
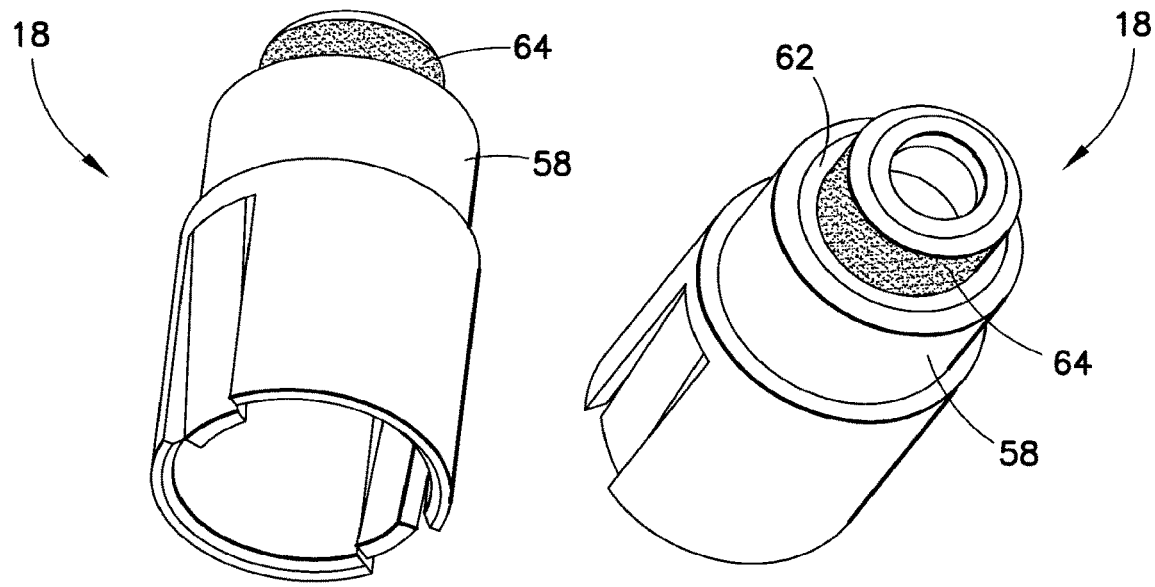

As shown in FIGS. 20 and 21, the second shield 20 may have an engagement edge 56 formed at the distal end 46 thereof. The engagement edge 56 is formed to be engaged by the first shield 18 such that movement of the first shield 18 is transmitted to the second shield 20. Also, the interengagement between the engagement edge 56 and the first shield 18 may limit distal movement of the first shield 18. The engagement edge 56 may be formed to prevent passage of the first shield 18 through the second shield 20, as shown in FIG. 21. Alternatively, as shown in FIGS. 43-45, the engagement edge 56 may be located at a mid-location in the second shield 20 with the engagement edge 56 allowing at least partial passage of the first shield 18 therethrough. The first shield 18 may be formed with the reduced diameter portion 58 shaped to pass through the opening 60 which may be defined by the engagement edge 56 (FIGS. 46-47). The shoulder 62 may be defined on the first shield 18 shaped to engage the engagement edge 56.

Figures 48, 49, 50:
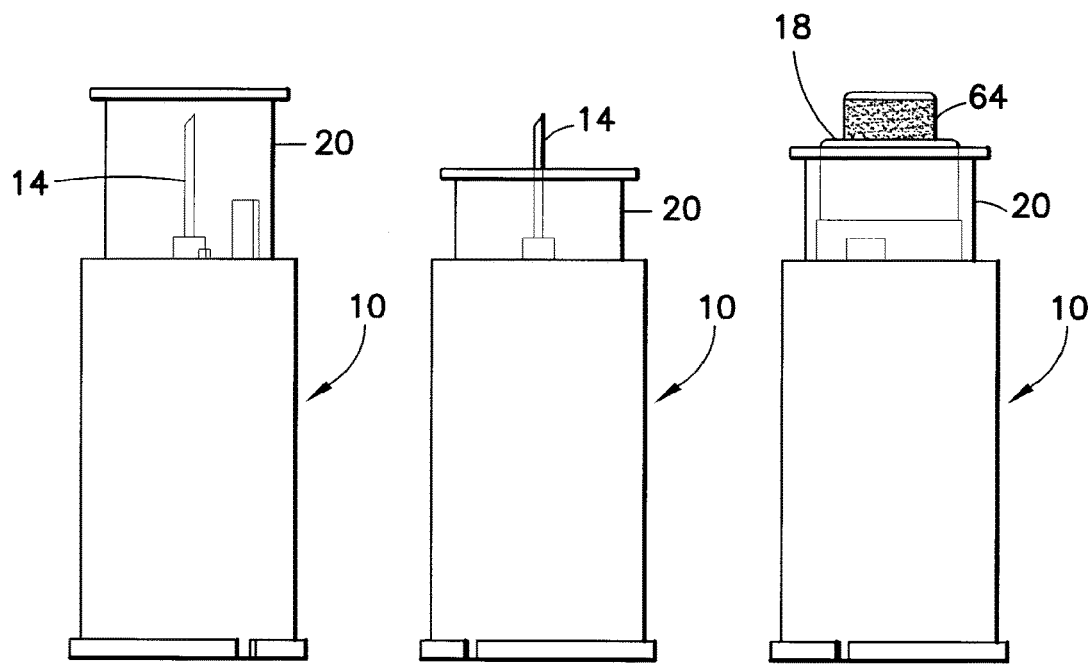

As shown in FIGS. 46 and 47, a use indication area 64 may be provided to provide visual indication that the assembly 10 has been used. The use indication area 64 may be used with any of the embodiments herein. For example, the use indication area 64 may be an area of colored and/or textured surface which becomes visible from the exterior of the assembly 10 when the assembly 10 reaches a final, after-use state. With the arrangement of FIGS. 46 and 47, the use indication area 64 may be provided on the reduced diameter portion 58 of the first shield 18. FIG. 50 shows the use indication area 64 being visually observable over the second shield 20 in a final, after-use state. In comparison, FIG. 48 shows the assembly 10 prior to use, and FIG. 49 shows the assembly 10 during use. The use indication area 64 is not visible prior to use or during use, only after use.

It is possible to make a portion of the second shield 20 transparent so that the use indication area 64 may be visible through a portion of the second shield 20. In this manner, the use indication area 64 may be used, for example, with the after-use arrangement of FIG. 20.

What is claimed is:
1. A safety needle assembly comprising:
a hub having a proximal end and a distal end;
a needle fixed to the hub, the needle having a distal end, formed for insertion into a patient, and a proximal end;
a first shield having a tubular body at least partially encircling a portion of the needle;
a second shield having a tubular body at least partially encircling a portion of the needle, wherein in an initial state, the second shield extends from the distal end of the hub;
biasing means disposed to urge the first shield distally toward the distal end of the needle; and
releasable retaining means for releasably retaining the first shield in a first state;
wherein upon a predetermined extent of proximal movement of the second shield relative to the hub, the retaining means releases the first shield, thereby allowing the biasing means to urge the first shield to a second state, the first and second shields covering the distal end of the needle in the second state;
wherein the releasable retaining means includes at least one deflectable tab, which extends inwardly from the hub to interferingly engage the first shield so as to retain the first shield in the first state against the force of the biasing means.

2. An assembly as in claim 1, wherein upon the second shield traversing the predetermined extent of proximal movement, the second shield causes the at least one tab to deflect outwardly thereby coming out of engagement with the first shield and allowing the first shield to be urged to the second state by the biasing means.

3. An assembly as in claim 1, wherein the first shield does not cover the distal end of the needle in the first state.

4. An assembly as in claim 1, wherein upon reaching the second state, a portion of the first shield interferingly engages the hub to maintain the first shield in the second state.

5. A safety needle assembly comprising:
a hub having a proximal end and a distal end;
a needle fixed to the hub, the needle having a distal end, formed for insertion into a patient, and a proximal end;
a first shield having a tubular body at least partially encircling a portion of the needle;
a second shield having a tubular body at least partially encircling a portion of the needle, wherein in an initial state, the second shield extends distally past the distal end of the hub;

biasing means disposed to urge the first shield distally toward the distal end of the needle; and releasable retaining means for releasably retaining the first shield in a first state;

wherein upon a predetermined extent of proximal movement of the second shield relative to the hub, the retaining means releases the first shield, thereby allowing the biasing means to urge the first shield to a second state, the first shield covering the distal end of the needle in the second state;

wherein the force of movement generated by the biasing means is transmitted to the second shield via the first shield;

wherein the first and second shields include cooperating elements allowing interengagement between the first and second shields; and wherein upon reaching the second state, a portion of the first shield interferingly engages the hub to maintain the first shield in the second state.

6. An assembly as in claim 5, wherein the first shield does not cover the distal end of the needle in the first state.

7. A safety needle assembly comprising:
a hub having a proximal end and a distal end;
a needle fixed to the hub, the needle having a distal end, formed for insertion into a patient, and a proximal end;
a first shield having a tubular body at least partially encircling a portion of the needle;
a second shield having a tubular body at least partially encircling a portion of the needle wherein, in an initial state, the second shield extends from the distal end of the hub;
biasing means disposed to urge the first shield distally toward the distal end of the needle; and
releasable retaining means for releasably retaining the first shield in a first state;
wherein upon a predetermined extent of proximal movement of the second shield relative to the hub, the retaining means releases the first shield, thereby allowing the biasing means to urge the first shield to a second state, the first and second shields covering the distal end of the needle in the second state; and
wherein the releasable retaining means includes at least one deflectable tab that extends inwardly from the hub and provides an interference fit between the first shield and the hub so as to retain the first shield in the first state against the force of the biasing means.

8. An assembly as in claim 7, wherein the first shield does not cover the distal end of the needle in the first state.

9. An assembly as in claim 7, wherein upon reaching the second state, a portion of the first shield interferingly engages the hub to maintain the first shield in the second state.

10. A safety needle assembly comprising:
a hub having a proximal end and a distal end;
a needle fixed to the hub, the needle having a distal end, formed for insertion into a patient, and a proximal end;
a first shield having a tubular body at least partially encircling a portion of the needle;
a second shield having a tubular body at least partially encircling a portion of the needle, wherein in an initial state, the second shield extends from the distal end of the hub;
biasing means disposed to urge the first shield distally toward the distal end of the needle; and
releasable retaining means for releasably retaining the first shield in a first state, wherein the releasable retaining means includes at least one deflectable tab disposed on the hub, the at least one tab extending inwardly and providing an interference fit with the first shield so as to retain the first shield in the first state against the force of the biasing means;
wherein upon a predetermined extent of proximal movement of the second shield relative to the hub and the first shield, the retaining means releases the first shield, thereby allowing the biasing means to urge the first shield to a second state, the first shield covering the distal end of the needle in the second state;
wherein the first shield is securable to the second shield;
wherein the biasing means generates sufficient force to overcome an-the interference fit between the first shield and the hub so as to separate the first shield from the hub with the first shield secured to the second shield; and
wherein upon reaching the second state, a portion of the first shield interferingly engages the hub to maintain the first shield in the second state.

11. An assembly as in claim 10, wherein the first shield does not cover the distal end of the needle in the first state.

12. A safety needle assembly comprising:
a hub having a proximal end and a distal end;
a needle fixed to the hub, the needle having a distal end, formed for insertion into a patient, and a proximal end;
a first shield having a tubular body at least partially encircling a portion of the needle;
a second shield having a tubular body at least partially encircling a portion of the needle, wherein in an initial state, the second shield extends from the distal end of the hub;
biasing means disposed to urge the first shield distally toward the distal end of the needle; and
releasable retaining means for releasably retaining the first shield in a first state;
wherein upon a predetermined extent of proximal movement of the second shield relative to the hub, the retaining means releases the first shield, thereby allowing the biasing means to urge the first shield to a second state, the first shield covering the distal end of the needle in the second state;
wherein the releasable retaining means includes at least one deflectable tab that extends inwardly from the hub and provides an interference fit between the first shield and the hub so as to retain the first shield in the first state against the force of the biasing means;
wherein the force of movement generated by the biasing means is transmitted to the second shield via the first shield;
wherein the first shield is securable to the second shield; and
wherein the biasing means generates sufficient force to overcome the interference fit so as to separate the first shield from the hub with the first shield secured to the second shield.

13. An assembly as in claim 12, wherein the first shield does not cover the distal end of the needle in the first state.

14. An assembly as in claim 12, wherein upon reaching the second state, a portion of the first shield interferingly engages the hub to maintain the first shield in the second state.

* * * * *